(12) United States Patent
Crystal et al.

(10) Patent No.: US 11,821,009 B2
(45) Date of Patent: Nov. 21, 2023

(54) GENETIC MODIFICATION OF THE AAV CAPSID RESULTING IN ALTERED TROPISM AND ENHANCED VECTOR DELIVERY

(71) Applicant: Cornell University, Ithaca, NY (US)

(72) Inventors: Ronald G. Crystal, New York, NY (US); Katie Stiles, Bronx, NY (US)

(73) Assignee: Cornell University, Ithaca, NY (US)

( * ) Notice: Subject to any disclaimer, the term of this patent is extended or adjusted under 35 U.S.C. 154(b) by 1226 days.

(21) Appl. No.: 16/411,906

(22) Filed: May 14, 2019

(65) Prior Publication Data

US 2020/0032220 A1  Jan. 30, 2020

Related U.S. Application Data

(60) Provisional application No. 62/671,777, filed on May 15, 2018.

(51) Int. Cl.
*C12N 7/00* (2006.01)
*A61K 39/23* (2006.01)
*A61K 35/761* (2015.01)

(52) U.S. Cl.
CPC .............. *C12N 7/00* (2013.01); *A61K 35/761* (2013.01); *C12N 2750/14121* (2013.01); *C12N 2750/14132* (2013.01); *C12N 2750/14141* (2013.01)

(58) Field of Classification Search
None
See application file for complete search history.

(56) References Cited

U.S. PATENT DOCUMENTS

| | | |
|---|---|---|
| 4,797,368 A | 1/1989 | Carter et al. |
| 4,863,457 A | 9/1989 | Lee |
| 5,378,475 A | 1/1995 | Smith et al. |
| 5,443,505 A | 8/1995 | Wong et al. |
| 5,464,758 A | 11/1995 | Gossen et al. |
| 5,814,618 A | 9/1998 | Bujard et al. |
| 6,342,390 B1 | 1/2002 | Wiener et al. |
| 6,491,907 B1 | 12/2002 | Rabinowitz et al. |
| 6,723,551 B2 | 4/2004 | Kotin et al. |
| 6,821,511 B2 | 11/2004 | Kotin et al. |
| 7,112,715 B2 | 9/2006 | Chambon et al. |
| 7,172,893 B2 | 2/2007 | Rabinowitz et al. |
| 7,314,912 B1 | 1/2008 | Hallek et al. |
| 7,892,809 B2 | 2/2011 | Bowles et al. |
| 8,476,418 B2 | 7/2013 | Mueller et al. |
| 8,663,624 B2 | 3/2014 | Schaffer et al. |

(Continued)

FOREIGN PATENT DOCUMENTS

| | | | |
|---|---|---|---|
| CN | 104470945 A * | 3/2015 | ............ A61K 38/16 |
| WO | WO-99/67393 A2 | 12/1999 | |

(Continued)

OTHER PUBLICATIONS

EPO English specification translation of CN104470945 (Year: 2016).*

(Continued)

*Primary Examiner* — M Franco G Salvoza

(74) *Attorney, Agent, or Firm* — Schwegman Lundberg & Woessner, P.A.

(57) ABSTRACT

Modified AAV vectors and uses thereof are provided.

19 Claims, 6 Drawing Sheets
(5 of 6 Drawing Sheet(s) Filed in Color)
Specification includes a Sequence Listing.

(56) References Cited

U.S. PATENT DOCUMENTS

| | | |
|---|---|---|
| 8,802,080 B2 | 8/2014 | Warrington et al. |
| 8,889,641 B2 | 11/2014 | Asokan et al. |
| 9,012,224 B2 | 4/2015 | Bowles et al. |
| 9,193,956 B2 | 11/2015 | Schaffer et al. |
| 9,409,953 B2 | 8/2016 | Asokan et al. |
| 9,457,103 B2 | 10/2016 | Schaffer et al. |
| 9,458,517 B2 | 10/2016 | Schaffer et al. |
| 9,475,845 B2 | 10/2016 | Asokan et al. |
| 9,587,282 B2 | 3/2017 | Schaffer et al. |
| 9,598,468 B2 | 3/2017 | Weigel-van Aken et al. |
| 9,624,274 B2 | 4/2017 | Lux et al. |
| 9,856,539 B2 | 1/2018 | Schaffer et al. |
| 10,047,128 B2 | 8/2018 | Judd et al. |
| 10,081,659 B2 | 9/2018 | Chiorini et al. |
| 10,202,657 B2 | 2/2019 | Schaffer et al. |
| 10,214,785 B2 | 2/2019 | Schaffer et al. |
| 2003/0053990 A1 | 3/2003 | Rabinowitz et al. |
| 2006/0088936 A1 | 4/2006 | Warrington et al. |
| 2006/0093589 A1 | 5/2006 | Warrington et al. |
| 2006/0188483 A1 | 8/2006 | Rabinowitz et al. |
| 2006/0188484 A1 | 8/2006 | Rabinowitz et al. |
| 2006/0292117 A1 | 12/2006 | Loiler et al. |
| 2007/0238684 A1 | 10/2007 | Hallek et al. |
| 2008/0269149 A1 | 10/2008 | Bowles et al. |
| 2009/0148411 A1 | 6/2009 | Warrington et al. |
| 2009/0148949 A1 | 6/2009 | Warrington et al. |
| 2009/0149414 A1 | 6/2009 | Warrington et al. |
| 2009/0215879 A1 | 8/2009 | Diprimio et al. |
| 2009/0286321 A1 | 11/2009 | Warrington et al. |
| 2011/0052617 A1 | 3/2011 | Hallek et al. |
| 2011/0104119 A1 | 5/2011 | Bowles et al. |
| 2012/0009268 A1 | 1/2012 | Asokan et al. |
| 2012/0164106 A1 | 6/2012 | Schaffer et al. |
| 2012/0202732 A1 | 8/2012 | Mueller et al. |
| 2013/0011432 A1* | 1/2013 | Crystal ............... A61P 25/30 530/410 |
| 2014/0093533 A1 | 4/2014 | Weigel-van Aken et al. |
| 2014/0242031 A1 | 8/2014 | Schaffer et al. |
| 2014/0294771 A1 | 10/2014 | Schaffer et al. |
| 2014/0364338 A1 | 12/2014 | Schaffer et al. |
| 2015/0005369 A1 | 1/2015 | Muzyczka et al. |
| 2015/0152142 A1 | 6/2015 | Asokan et al. |
| 2015/0225702 A1 | 8/2015 | Schaffer et al. |
| 2015/0232953 A1 | 8/2015 | Schaffer et al. |
| 2016/0184394 A1 | 6/2016 | Schaffer et al. |
| 2016/0289275 A1 | 10/2016 | Chiorini et al. |
| 2016/0369298 A1 | 12/2016 | Marsic et al. |
| 2016/0375151 A1 | 12/2016 | Schaffer et al. |
| 2016/0376323 A1 | 12/2016 | Schaffer et al. |
| 2017/0044504 A1 | 2/2017 | Schaffer et al. |
| 2018/0127471 A1 | 5/2018 | Keravala |
| 2018/0135074 A1 | 5/2018 | Srivastava et al. |
| 2018/0208943 A1 | 7/2018 | Schmidt |
| 2021/0363192 A1* | 11/2021 | Anguela ............... C12N 7/00 |

FOREIGN PATENT DOCUMENTS

| | | | |
|---|---|---|---|
| WO | WO-00/28004 A1 | 5/2000 | |
| WO | WO-03/089612 A2 | 10/2003 | |
| WO | WO-2004/027019 A2 | 4/2004 | |
| WO | WO-2004/099423 A1 | 11/2004 | |
| WO | WO-200/6066066 A2 | 6/2006 | |
| WO | WO-2009/108274 A2 | 9/2009 | |
| WO | WO-2010/093784 A2 | 8/2010 | |
| WO | WO-2010/127097 A1 | 11/2010 | |
| WO | WO-2010/136549 A2 | 12/2010 | |
| WO | WO-2012/145601 A2 | 10/2012 | |
| WO | WO-2012/159006 A2 | 11/2012 | |
| WO | WO-2015/048534 A1 | 4/2015 | |
| WO | WO-2016/134338 A1 | 8/2016 | |
| WO | WO-2016134338 A1 * | 8/2016 | ............. A61K 35/76 |
| WO | WO-2017/192699 A1 | 11/2017 | |
| WO | WO-2018/022608 A2 | 2/2018 | |
| WO | WO-2018/075798 A1 | 4/2018 | |
| WO | WO-2018/156654 A1 | 8/2018 | |
| WO | WO-2018/222503 A1 | 12/2018 | |
| WO | WO-2019/006182 A1 | 1/2019 | |

OTHER PUBLICATIONS

Bantel-Schaal, Ursula, et al., "Human Adeno-Associated Virus Type 5 Is Only Distantly Related to Other Known Primate Helper-Dependent Parvoviruses", Journal of Virology, 73(2), (1999), 939-947.

Carter, Brian J, "Adeno-Associated Virus Vectiors in Clinical Trials", Human Gene Therapy, 16(5), (2005), 541-550.

Cearley, Cassia N., et al., "Transduction characteristics of adeno-associated virus vectors expressing cap serotypes 7, 8, 9, and Rh10 in the mouse brain", Molecular Therapy, 13(3), (2006), 528-537.

Chan, Ken Y., et al., "Engineered AAVs for efficient noninvasive gene delivery to the central and peripheral nervous systems", Nature Neuroscience, 20, (2017), 1172-1179.

Chiorini, J. A., et al., "Cloning and Characterization of Adeno-Associated Virus Type 5", Journal of Virology, 73(2), (1999), 1309-1319.

Chiorini, J. A., et al., "Cloning of adeno-associated virus type 4 (AAV4) and generation of recombinant AAV4 particles.", Journal of Virology, 71(9), (1997), 6823-6833.

Dalkara, Deniz, et al., "In Vivo-Directed Evolution of a New Adeno-Associated Virus for Therapeutic Outer Retinal Gene Delivery from the Vitreous", Sci Transl Med, 5(189), (2013), 1-11.

De, Bishnu P., et al., "High Levels of Persistent Expression of α1-Antitrypsin Mediated by the Nonhuman Primate Serotype rh. 10 Adeno-associated Virus Despite Preexisting Immunity to Common Human Adeno-associated Viruses", Mol. Ther., 13(1), (Jan. 2006), 67-76.

Diprimo, N., et al., "Surface Loop Dynamics in Adeno-Associated Virus Capsid Assembly", Journal of Virology, 82(11), (Jun. 2008), 5178-5189.

Flotte, Terence R., et al., "New AAV Serotypes May Broaden the Therapeutic Pipeline to Human Gene Therapy", Molecular Therapy, 13(1), (Jan. 2006), 1-2.

Gao, G., et al., "Clades of Adeno-Associated Viruses Are Widely Disseminated in Human Tissues", Journal of Virology, 78(12), (2004), 6381-6388.

Gao, Guangping, et al., "Biology of AAV Serotype Vectors in Liver-Directed Gene Transfer to Nonhuman Primates", Molecular Therapy, 13(1), (2006), 77-87.

Gao, Guang-Ping, et al., "Novel adeno-associated viruses from rhesus monkeys as vectors for human gene therapy", Proc. Natl. Acad. Sci., USA, 99(18), (2002), 11854-11859.

Govindasamy, Lakshmanan, et al., "Structural Insights into Adeno-Associated Virus Serotype 5", Journal of Virology, 87(20), (Oct. 2013), 11187-11199.

Grimm, Dirk, et al., "In Vitro and In Vivo Gene Therapy Vector Evolution via Multispecies Interbreeding and Retargeting of Adeno-Associated Viruses", Journal of Virology, 82(12), (Jun. 2008), 5887-5911.

Hida, Kaoru, et al., "Sites in the AAV5 capsid tolerant to deletions and tandem duplications", Archives of Biochemistry and Biophysics, 496(1), (2010), 1-8.

Im, Dong-Soo, et al., "The AAV Origin Binding Protein Rep68 is an ATP-Dependent Site-Specific Endonuclease with DNA Helicase Activity", Cell, 61(3), (1990), 447-457.

Judd, Justin, et al., "Random Insertion of mCherry Into VP3 Domain of Adeno-associated Virus Yields Fluorescent Capsids With no Loss of Infectivity", Molecular Therapy Nucleic Acids. vol. 1: e54, (2012), 1-10.

Khabou, Hanen, et al., "Insight Into the Mechanisms of Enhanced Retinal Transduction by the Engineered AAV2 Capsid Variant -7m8", Biotechnology and Bioengineering. 113(12), (Dec. 2016), 2712-2724.

Kramer, Beat P., et al., "Chapter 11—Transgene Control Engineering in Mammalian Cells", In: Methods in Molecular Biology, vol. 308: Therapeutic Proteins—Methods and Protocols, edited by C. Mark Smales, et al., Humana Press, Inc., (2005), 123-143.

(56) References Cited

OTHER PUBLICATIONS

Levy, Hazel C., et al., "Heparin binding induces conformational changes in Adeno-associated virus serotype 2", Journal of Structural Biology, 165, (2009), 146-156.

Mao, Yanxiong, et al., "Persistent Suppression of Ocular Neovascularization with (Intravitreal Administration of AAVrh. 10 Coding for Bevacizumab", Human Gene Ther., 22(12), (2011), 1525-1535.

No, David, et al., "Ecdysone-Inducible Gene Expression in Mammalian Cells and Transgenic Mice", Proc. Natl. Acad. Sci. USA, 93(8), (1996), 3346-3351.

Opie, Shaun R., et al., "Identi?cation of Amino Acid Residues in the Capsid Proteins of Adeno-Associated Virus Type 2 That Contribute to Heparan Sulfate Proteoglycan Binding", Journal of Virology, 77(12), (Jun. 2003), 6995-7006.

Pereira, Daniel J., et al., "The Adeno-Associated Virus (AAV) Rep Protein Acts as both a Repressor and an Activator To Regulate AAV Transcription during a Productive Infection", Journal of Virology, 71(2). (1997), 1079-1088.

Rutledge, Elizabeth A., et al., "Infectious Clones and Vectors Derived from Adeno-Associated Virus (AAV) Serotypes Other Than AAV Type 2", Journal of Virology, 72(1), (Jan. 1998), 309-319.

Srivastava, Arun, et al., "Nucleotide Sequence and Organization of the Adeno-Associated Virus 2 Genome", Journal of Virology, 45(2), (1983), 555-564.

Stiles, Katie M., et al., "Genetc Modification of the AAV5 Capsid Resulting in De-targeted Liver and Enhanced Vector Delivery to Lung Following Intravenous Administration", (Abstract), American Society of Gene & Cell Therapy, 21st Annual Meeting, Chicago, IL, (2018), 2 pgs.

Watanabe, M., et al., "AAVrh. 10-mediated genetic delivery of bevacizumab to the pleura to provide local anti-VEGF to suppress growth of metastatic lung tumors", Gene Therapy, 17(8), (2010), 1042-1051.

Wright, J. F., et al., "Recombinant adeno-associated virus: Formulation challenges and strategies for a gene therapy vector", (Abstract), Curr. Opin. Drug Discov. Devel., 6(2). (2003), 174-178, (2003), 1 pg.

Wright, J. Fraser, et al., "Identification of Factors that Contribute to Recombinant AAV2 Particle Aggregation and Methods to Prevent Its Occurrence during Vector Purification and Formulation", Molecular Therapy, 12(1), (Jul. 2005), 171-178.

Wu, Pei, et al., "Mutational Analysis of the Adeno-Associated Virus Type 2 (AAV2) Capsid Gene and Construction of AAV2 Vectors with Altered Tropism", Journal of Virology, 74(18), (Sep. 2000), 8635-8647.

Wu, Z., et al., "Adeno-associated Virus Serotypes: Vector Toolkit for Human Gene Therapy", Molecular Therapy, 14(3), (Sep. 2006), 316-327.

Zabner, Joseph, et al., "Adeno-Associated Virus Type 5 (AAV5) but Not AAV2 Binds to the Apical Surfaces of Airway Epithelia and Facilitates Gene Transfer", Journal of Virology, 74(8), (Apr. 2000), 3852-3858.

* cited by examiner

Capsid Monomer

AAV5 Capsid

AAV5-PK2-AAT vector

```
                        SEQUENCE LISTING

<160> NUMBER OF SEQ ID NOS: 23

<210> SEQ ID NO 1
<211> LENGTH: 32
<212> TYPE: PRT
<213> ORGANISM: Adeno-associated virus

<400> SEQUENCE: 1

Leu Ser Arg Thr Asn Thr Pro Ser Gly Thr Thr Thr Gln Ser Arg Leu
1               5                   10                  15

Gln Phe Ser Gln Ala Gly Ala Ser Asp Ile Arg Asp Gln Ser Arg Asn
            20                  25                  30

<210> SEQ ID NO 2
<211> LENGTH: 26
<212> TYPE: PRT
<213> ORGANISM: Adeno-associated virus

<400> SEQUENCE: 2

Phe Val Ser Thr Asn Asn Thr Gly Gly Val Gln Phe Asn Lys Asn Leu
1               5                   10                  15

Ala Gly Arg Tyr Ala Asn Thr Tyr Lys Asn
            20                  25

<210> SEQ ID NO 3

<400> SEQUENCE: 3

000

<210> SEQ ID NO 4
<211> LENGTH: 13
<212> TYPE: PRT
<213> ORGANISM: Adeno-associated virus

<400> SEQUENCE: 4

Thr Asn Asn Gln Ser Ser Thr Thr Ala Pro Ala Thr Gly
1               5                   10

<210> SEQ ID NO 5
<211> LENGTH: 14
<212> TYPE: PRT
<213> ORGANISM: Artificial Sequence
```

```
<220> FEATURE:
<223> OTHER INFORMATION: A synthetic amino acid sequence

<400> SEQUENCE: 5

Thr Asn Leu Gln Lys Arg Gly Asn Arg Gln Ala Ala Thr Ala
1               5                   10

<210> SEQ ID NO 6
<211> LENGTH: 15
<212> TYPE: PRT
<213> ORGANISM: Artificial Sequence
<220> FEATURE:
<223> OTHER INFORMATION: A synthetic amino acid sequence

<400> SEQUENCE: 6

Thr Asn Leu Lys Lys Gln Arg Gly Asn Arg Gln Ala Ala Thr Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: A synthetic amino acid sequence

<400> SEQUENCE: 7

Thr Asn Leu Lys Gln Arg Gly Lys Asn Arg Gln Ala Ala Thr Ala
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: A synthetic amino acid sequence

<400> SEQUENCE: 8

Thr Asn Leu Lys Gln Arg Gly Asn Arg Lys Gln Ala Ala Thr Ala
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: A synthetic amino acid sequence

<400> SEQUENCE: 9

Thr Asn Asn Gln Lys Ser Ser Thr Thr Ala Pro Ala Thr Gly
1               5                   10

<210> SEQ ID NO 10
<211> LENGTH: 15
<212> TYPE: PRT
<213> ORGANISM: Artificial Sequence
<220> FEATURE:
<223> OTHER INFORMATION: A synthetic amino acid sequence

<400> SEQUENCE: 10

Thr Asn Asn Gln Lys Lys Ser Ser Thr Thr Ala Pro Ala Thr Gly
1               5                   10                  15

<210> SEQ ID NO 11
<211> LENGTH: 15
<212> TYPE: PRT
<213> ORGANISM: Artificial Sequence
<220> FEATURE:
```

```
<223> OTHER INFORMATION: A synthetic amino acid sequence

<400> SEQUENCE: 11

Thr Asn Asn Gln Lys Ser Ser Thr Thr Lys Ala Pro Ala Thr Gly
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: A synthetic amino acid sequence

<400> SEQUENCE: 12

Thr Asn Lys Asn Gln Ser Ser Thr Thr Ala Pro Ala Thr Gly
1               5                   10

<210> SEQ ID NO 13
<211> LENGTH: 15
<212> TYPE: PRT
<213> ORGANISM: Artificial Sequence
<220> FEATURE:
<223> OTHER INFORMATION: A synthetic amino acid sequence

<400> SEQUENCE: 13

Thr Asn Lys Lys Asn Gln Ser Ser Thr Thr Ala Pro Ala Thr Gly
1               5                   10                  15

<210> SEQ ID NO 14

<400> SEQUENCE: 14

000

<210> SEQ ID NO 15
<211> LENGTH: 15
<212> TYPE: PRT
<213> ORGANISM: Artificial Sequence
<220> FEATURE:
<223> OTHER INFORMATION: A synthetic amino acid sequence

<400> SEQUENCE: 15

Thr Asn Lys Asn Gln Ser Ser Thr Thr Ala Lys Pro Ala Thr Gly
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: A synthetic amino acid sequence

<400> SEQUENCE: 16

Thr Asn Lys Asn Gln Ser Ser Lys Thr Ala Pro Ala Thr Gly
1               5                   10                  15

<210> SEQ ID NO 17
<211> LENGTH: 735
<212> TYPE: PRT
<213> ORGANISM: Adeno-associated virus

<400> SEQUENCE: 17

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30
```

```
Lys Pro Ala Glu Arg His Lys Asp Asp Ser Arg Gly Leu Val Leu Pro
             35                  40                  45

Gly Tyr Lys Tyr Leu Gly Pro Phe Asn Gly Leu Asp Lys Gly Glu Pro
 50                  55                  60

Val Asn Glu Ala Asp Ala Ala Leu Glu His Asp Lys Ala Tyr Asp
 65              70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
             115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445
```

```
Asn Thr Pro Ser Gly Thr Thr Thr Gln Ser Arg Leu Gln Phe Ser Gln
            450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
            515                 520                 525
Asp Glu Glu Lys Phe Phe Pro Gln Ser Gly Val Leu Ile Phe Gly Lys
530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
            580                 585                 590
Ala Asp Val Asn Thr Gln Gly Val Leu Pro Gly Met Val Trp Gln Asp
            595                 600                 605
Arg Asp Val Tyr Leu Gln Gly Pro Ile Trp Ala Lys Ile Pro His Thr
610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
            660                 665                 670
Tyr Ser Thr Gly Gln Val Ser Val Glu Ile Glu Trp Glu Leu Gln Lys
            675                 680                 685
Glu Asn Ser Lys Arg Trp Asn Pro Glu Ile Gln Tyr Thr Ser Asn Tyr
690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735

<210> SEQ ID NO 18
<211> LENGTH: 738
<212> TYPE: PRT
<213> ORGANISM: Adeno-associated virus

<400> SEQUENCE: 18

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Gln Ala Gly Asp Asn Pro Tyr Leu Arg Tyr Asn His Ala
                85                  90                  95
```

-continued

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510
```

```
Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
            565                 570                 575

Glu Glu Tyr Gly Ile Val Ala Asp Asn Leu Gln Gln Gln Asn Thr Ala
                580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 19
<211> LENGTH: 737
<212> TYPE: PRT
<213> ORGANISM: Adeno-associated virus

<400> SEQUENCE: 19

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140
```

```
Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
            165                 170                 175

Thr Gly Asp Ser Glu Ser Val Pro Asp Pro Gln Pro Leu Gly Glu Pro
        180                 185                 190

Pro Ala Ala Pro Ser Ser Val Gly Ser Gly Thr Val Ala Ala Gly Gly
    195                 200                 205

Gly Ala Pro Met Ala Asp Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asn Pro Gly Gly Thr Ala Gly Asn Arg Glu Leu Gln
450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
    530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
```

-continued

```
                565                 570                 575

Glu Tyr Gly Ile Val Ser Ser Asn Leu Gln Ala Asn Thr Ala Ala
                580                 585                 590

Gln Thr Gln Val Val Asn Asn Gln Gly Ala Leu Pro Gly Met Val Trp
                595                 600                 605

Gln Asn Arg Asp Val Tyr Leu Gln Gly Pro Ile Trp Ala Lys Ile Pro
610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
                660                 665                 670

Thr Gln Tyr Ser Thr Gly Gln Val Ser Val Glu Ile Glu Trp Glu Leu
                675                 680                 685

Gln Lys Glu Asn Ser Lys Arg Trp Asn Pro Glu Ile Gln Tyr Thr Ser
                690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 20
<211> LENGTH: 724
<212> TYPE: PRT
<213> ORGANISM: Adeno-associated virus

<400> SEQUENCE: 20

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
                20                  25                  30

Pro Asn Gln Gln His Gln Asp Gln Ala Arg Gly Leu Val Leu Pro Gly
            35                  40                  45

Tyr Asn Tyr Leu Gly Pro Gly Asn Gly Leu Asp Arg Gly Glu Pro Val
        50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
                100                 105                 110

Leu Gly Lys Ala Val Phe Gln Ala Lys Lys Arg Val Leu Glu Pro Phe
            115                 120                 125

Gly Leu Val Glu Glu Gly Ala Lys Thr Ala Pro Thr Gly Lys Arg Ile
        130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
                180                 185                 190

Met Ser Ala Gly Gly Gly Gly Pro Leu Gly Asp Asn Asn Gln Gly Ala
```

```
            195                 200                 205
Asp Gly Val Gly Asn Ala Ser Gly Asp Trp His Cys Asp Ser Thr Trp
210                 215                 220
Met Gly Asp Arg Val Val Thr Lys Ser Thr Arg Thr Trp Val Leu Pro
225                 230                 235                 240
Ser Tyr Asn Asn His Gln Tyr Arg Glu Ile Lys Ser Gly Ser Val Asp
                245                 250                 255
Gly Ser Asn Ala Asn Ala Tyr Phe Gly Tyr Ser Thr Pro Trp Gly Tyr
                260                 265                 270
Phe Asp Phe Asn Arg Phe His Ser His Trp Ser Pro Arg Asp Trp Gln
                275                 280                 285
Arg Leu Ile Asn Asn Tyr Trp Gly Phe Arg Pro Arg Ser Leu Arg Val
                290                 295                 300
Lys Ile Phe Asn Ile Gln Val Lys Glu Val Thr Val Gln Asp Ser Thr
305                 310                 315                 320
Thr Thr Ile Ala Asn Asn Leu Thr Ser Thr Val Gln Val Phe Thr Asp
                325                 330                 335
Asp Asp Tyr Gln Leu Pro Tyr Val Val Gly Asn Gly Thr Glu Gly Cys
                340                 345                 350
Leu Pro Ala Phe Pro Pro Gln Val Phe Thr Leu Pro Gln Tyr Gly Tyr
                355                 360                 365
Ala Thr Leu Asn Arg Asp Asn Thr Glu Asn Pro Thr Glu Arg Ser Ser
370                 375                 380
Phe Phe Cys Leu Glu Tyr Phe Pro Ser Lys Met Leu Arg Thr Gly Asn
385                 390                 395                 400
Asn Phe Glu Phe Thr Tyr Asn Phe Glu Glu Val Pro Phe His Ser Ser
                405                 410                 415
Phe Ala Pro Ser Gln Asn Leu Phe Lys Leu Ala Asn Pro Leu Val Asp
                420                 425                 430
Gln Tyr Leu Tyr Arg Phe Val Ser Thr Asn Asn Thr Gly Gly Val Gln
                435                 440                 445
Phe Asn Lys Asn Leu Ala Gly Arg Tyr Ala Asn Thr Tyr Lys Asn Trp
450                 455                 460
Phe Pro Gly Pro Met Gly Arg Thr Gln Gly Trp Asn Leu Gly Ser Gly
465                 470                 475                 480
Val Asn Arg Ala Ser Val Ser Ala Phe Ala Thr Thr Asn Arg Met Glu
                485                 490                 495
Leu Glu Gly Ala Ser Tyr Gln Val Pro Pro Gln Pro Asn Gly Met Thr
                500                 505                 510
Asn Asn Leu Gln Gly Ser Asn Thr Tyr Ala Leu Glu Asn Thr Met Ile
                515                 520                 525
Phe Asn Ser Gln Pro Ala Asn Pro Gly Thr Thr Ala Thr Tyr Leu Glu
                530                 535                 540
Gly Asn Met Leu Ile Thr Ser Glu Ser Glu Thr Gln Pro Val Asn Arg
545                 550                 555                 560
Val Ala Tyr Asn Val Gly Gly Gln Met Ala Thr Asn Asn Gln Ser Ser
                565                 570                 575
Thr Thr Ala Pro Ala Thr Gly Thr Tyr Asn Leu Gln Glu Ile Val Pro
                580                 585                 590
Gly Ser Val Trp Met Glu Arg Asp Val Tyr Leu Gln Gly Pro Ile Trp
                595                 600                 605
Ala Lys Ile Pro Glu Thr Gly Ala His Phe His Pro Ser Pro Ala Met
610                 615                 620
```

```
Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
            645                 650                 655

Ser Phe Ile Thr Gln Tyr Ser Thr Gly Gln Val Thr Val Glu Met Glu
        660                 665                 670

Trp Glu Leu Lys Lys Glu Asn Ser Lys Arg Trp Asn Pro Glu Ile Gln
            675                 680                 685

Tyr Thr Asn Asn Tyr Asn Asp Pro Gln Phe Val Asp Phe Ala Pro Asp
        690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 21
<211> LENGTH: 724
<212> TYPE: PRT
<213> ORGANISM: Adeno-associated virus

<400> SEQUENCE: 21

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270
```

-continued

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
        290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
                340                 345                 350

Leu Pro Ala Phe Pro Pro Gln Val Phe Thr Leu Pro Gln Tyr Gly Tyr
                355                 360                 365

Ala Thr Leu Asn Arg Asp Asn Thr Glu Asn Pro Thr Glu Arg Ser Ser
        370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
                420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
                500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
        530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
                580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
        610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
                660                 665                 670

Trp Glu Leu Lys Lys Glu Asn Ser Lys Arg Trp Asn Pro Glu Ile Gln
        675                 680                 685

```
Tyr Thr Asn Asn Tyr Asn Asp Pro Gln Phe Val Asp Phe Ala Pro Asp
    690             695                 700
Ser Thr Gly Glu Tyr Arg Thr Thr Arg Pro Ile Gly Thr Arg Tyr Leu
705             710                 715                 720
Thr Arg Pro Leu

<210> SEQ ID NO 22
<211> LENGTH: 13
<212> TYPE: PRT
<213> ORGANISM: Artificial Sequence
<220> FEATURE:
<223> OTHER INFORMATION: A synthetic amino acid sequence
<221> NAME/KEY: SITE
<222> LOCATION: (1)...(13)
<223> OTHER INFORMATION: Xaa = A, G, L, V, T, I, S, M, D, E, N, Q, H, P,
      or Y

<400> SEQUENCE: 22

Xaa Xaa Xaa Xaa Xaa Xaa Xaa Xaa Xaa Xaa Xaa Xaa Xaa
1               5                   10

<210> SEQ ID NO 23
<211> LENGTH: 13
<212> TYPE: PRT
<213> ORGANISM: Artificial Sequence
<220> FEATURE:
<223> OTHER INFORMATION: A synthetic amino acid sequence
<221> NAME/KEY: SITE
<222> LOCATION: (1)...(13)
<223> OTHER INFORMATION: Xaa = A, G, V, T, I, S, L, M, C, D, E, N, Q, H,
      P, Y, W or F

<400> SEQUENCE: 23

Xaa Xaa Xaa Xaa Xaa Xaa Xaa Xaa Xaa Xaa Xaa Xaa Xaa
1               5                   10
```

GENETIC MODIFICATION OF THE AAV CAPSID RESULTING IN ALTERED TROPISM AND ENHANCED VECTOR DELIVERY

CROSS-REFERENCE TO RELATED APPLICATIONS

This application claims the benefit of the filing date of U.S. application No. 62/671,777, filed on May 15, 2018, the disclosure of which is incorporated by reference herein.

SUMMARY

Intravenous administration of all naturally occurring adeno-associated virus (AAV) vectors are liver tropic, with the majority of the total vector dose mediating gene expression in liver hepatocytes. To design an AAV vector to de-target liver but enhance delivery to lung following intravenous administration, additional positively charged residues, e.g., lysine residues, were added to the AAV capsid to enhance the ability of the virus to adhere to negatively charged cell surface molecules such as heparan sulfate proteoglycans, leading to enhanced transduction of the organ representing the first capillary bed encountered. For example, site-directed mutagenesis was used to insert two lysine residues into variable loop VIII of the AAV serotype 5 capsid of a vector coding for human α1-antitrypsin (AAV5-PK2-hAAT). Distribution of the vector and vector expression was quantified following administration of $10^{11}$ genome copies (gc) of AAV5-PK2-hAAT or the identical vector with the AAV5 wildtype capsid (AAV5-hAAT) by the intravenous route to C57Bl/6 male mice. Four weeks post-administration, organs were harvested, and vector DNA and mRNA quantified by TaqMan. Consistent with the experience for all naturally occurring AAV vectors, intravenous administration of AAV5-hAAT resulted in the highest vector DNA and mRNA levels in the liver. In striking contrast, following intravenous administration of the AAV5-PK2-hAAT vector, the amount of vector DNA and hAAT mRNA in the liver was significantly reduced. The lysine-modified vector was de-targeted from the liver, resulting in 59-fold lower liver and 1.8-fold higher lung vector DNA levels compared to the wild-type capsid. The hAAT mRNA levels paralleled the vector DNA levels. Serum AAT levels were 84±20 μg/mL for AAV5-hAAT and only 0.54±0.16 μg/mL for AAV5-PK2-hAAT supporting the de-targeting of AAV5-PK2-hAAT to the liver, the main producer of secreted proteins such as hAAT. Thus, genetic modification of the AAV capsid with positively charged residues, for example lysine residues, shifts the targeting of the vector away from the liver potentially by increasing transduction of the first capillary bed encountered following intravenous administration (e.g., the lung). This "sticky" capsid modification strategy with positively charged residues such as lysine residues is likely applicable to all AAV vectors and, depending on the administration route, useful for targeting AAV vectors to specific organs, and also useful from a safety viewpoint for limiting "spill" of vector to the systemic circulation and other organs.

In one embodiment, the disclosure provides for an infectious recombinant adeno-associated virus (AAV) with altered tropism, comprising: a modified viral capsid that provides the altered tropism, which capsid is altered relative to a corresponding virus without the modification in the viral capsid, wherein the modified viral capsid comprises i) an insertion of one or more positively charged amino acid residues in a portion of the capsid that is exposed to the surface, or ii) a substitution of one or more non-positively charged amino acid residues with one or more positively charged amino acid residues in a portion of the capsid that is exposed to the surface. In one embodiment, the modification decreases liver tropism. In one embodiment, at least one of the positively charged residues is a lysine. In one embodiment, the capsid comprises the substitution of one or more non-positively charged amino acid residues with one or more positively charged amino acid residues. In one embodiment, 2, 3, 4, 5, 6, 7, 8, 9, 10 or up to 20 amino acids are substituted. In one embodiment, 5 or fewer amino acids are substituted with positively charged amino acid residues. In one embodiment, 4 or fewer amino acids are substituted with positively charged amino acid residues. In one embodiment, the capsid comprises an insertion of one or more positively charged amino acid residues. In one embodiment, the insertion comprises 2, 3, 4, 5, 6, 7, 8, 9, 10 or up to 20 amino acids. In one embodiment, 5 or fewer amino acids are inserted. In one embodiment, 4 or fewer amino acids are inserted. In one embodiment, the substituted sequence or the insertion does not result in a capsid that has enhanced retinal cell binding. In one embodiment, the substituted sequence or the insertion does not result in a capsid that has enhanced cardiomyocyte binding. In one embodiment, the substituted sequence or the insertion does not result in a capsid that has altered antigenicity or has enzymatic activity. In one embodiment, the substituted sequence does not result in a capsid that has a corresponding sequence of a different AAV serotype. In one embodiment, two or more positively charged amino acid residues are substituted or inserted. In one embodiment, at least two of the positively charged residues are adjacent. In one embodiment, the positively charged residues are not adjacent. In one embodiment, the positively charged residue comprises lysine, histidine or arginine. In one embodiment, the modification comprises one or two lysine residues. In one embodiment, the modification comprises a mixture of lysine, histidine or arginine residues, or any combination thereof. In one embodiment, the modification comprises a mixture of lysine and arginine residues. In one embodiment, the modification comprises lysine residues. In one embodiment, the AAV is AAV2, AAV3, AAV4, AAV5, AAV6, AAV7, AAV8, AAV9, or AAVrh10. In one embodiment, the AAV that is modified is not AAV2. In one embodiment, the AAV that is modified is AAV5. In one embodiment, the AAV genome is a recombinant genome having at least one expression cassette for an exogenous gene product. In one embodiment, the exogenous gene product is a prophylactic or therapeutic gene product. In one embodiment, the modification is in loop IV or loop VIII of the capsid. Loop IV is also referred to as GH-L1 and loop VIII is also referred to as GH-L5. In general loop IV corresponds to residues 445-476 (AAV2 numbering) and loop VIII corresponds to residues 580-592 (AAV2 numbering) in VP1. For example, in one embodiment, unmodified loop IV in AAV2 has the following sequence: LSRTNTPSGTTTQSRLQFSQAGASDIRDQSRN (SEQ ID NO:1); unmodified loop IV in AAV5 has the following sequence: FVSTNNTGGVQFNKNLAGRYANTYKN (SEQ ID NO:2); unmodified loop VIII in AAV2 has the following sequence: (SEQ ID NO:3); and unmodified loop VIII in AAV5 has the following sequence: TNNQSSTTAPATG (SEQ ID NO:4). Exemplary insertions in loop VIII (insertions are underlined) include but are not limited to: for AAV2, TNLQ<u>K</u>RGNRQAATA (SEQ ID NO:5), TNL<u>KK</u>QRGNRQAATA (SEQ ID NO:6), TNL<u>K</u>QRG<u>K</u>NRQAATA (SEQ ID NO:7), or TNL<u>K</u>QRGNR<u>K</u>QAATA (SEQ ID NO:8), and for AAV5, TNNQ<u>K</u>SSTTAPATG (SEQ ID NO:9), TNNQKKSSTTAPATG (SEQ ID NO:10), TNNQ KSSTTKAPATG (SEQ ID NO:11), TNKNQSSTTAPATG (SEQ ID NO:12), TNKKNQSSTTAPATG (SEQ ID NO:13), TNKNQSSTTAKPATG (SEQ ID NO:15 or TNKNQSS KTAPATG (SEQ ID NO:16).

Also provided is a method to prevent, inhibit or treat a disorder or disease in a mammal, comprising administering to a mammal in need thereof a composition comprising an amount of the modified AAV effective to prevent, inhibit or treat the disorder or disease. In one embodiment, the mammal is a human. In one embodiment, the composition is systemically administered. In one embodiment, the composition is intravenously administered. In one embodiment, wherein one or more lysine residues are inserted at a position corresponding to position 570 to 580 in an AAV5 capsid protein. In one embodiment, the capsid modification enhances delivery to an organ other than liver. In one embodiment, the modification enhances delivery to the lung. In one embodiment, the modification enhances delivery to an organ that is different than the virus without the modification. In one embodiment, the AAV is AAV2, AAV3, AAV4, AAV5, AAV6, AAV7, AAV8, or AAVrh10. In one embodiment, the AAV that is modified is not AAV2. In one embodiment, the AAV that is modified is AAV5. In one embodiment, the modified AAV delivers a prophylactic or a therapeutic gene, e.g., one encoding alpha 1-antitrypsin, e.g., human alpha 1-antitrypsin, factor VIII, factor IX, aromatic L-amino acid decarboxylase, adenosine deaminase, cystic fibrosis transmembrane receptor, dystrophin, beta-globin, lipoprotein lipase, a cytokine, a growth factor, a tumor suppressor, a microbial antigen, a monoclonal antibody, a nuclease, a pathogen antigen, an immune response modulator, or a cytotoxic gene product. A dose of the viral vector may be about $1 \times 10^{11}$ to about $1 \times 10^{16}$ genome copies, about $1 \times 10^{12}$ to about $1 \times 10^{15}$ genome copies about $1 \times 10^{11}$ to about $1 \times 10^{13}$ genome copies, or about $1 \times 10^{13}$ to about $1 \times 10^{15}$ genome copies.

BRIEF DESCRIPTION OF FIGURES

The patent or application file contains at least one drawing executed in color. Copies of this patent or patent application publication with color drawing(s) will be provided by the Office upon request and payment of the necessary fee.

DETAILED DESCRIPTION

Definitions

Figure 1A:
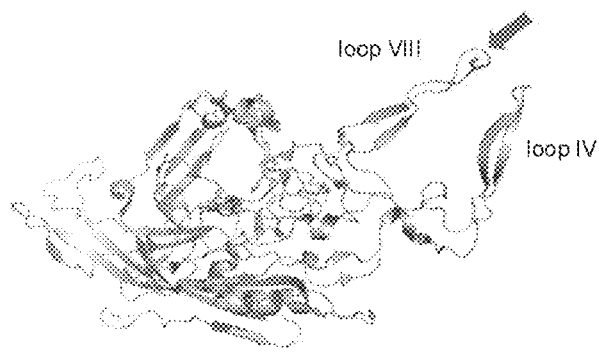
FIGS. 1A-D. Polylysine insertion into AAV5 capsid. A) Ribbon diagram representation of AAV5 VP3 monomer. Amino acid 575 is highlighted in red and polylysine insertion site indicated with green arrow. B) 3D rendering of AAV5 capsid with amino acid 575 highlighted in red. C) AAV5-PK2-AAT construct. The expression cassette including the AAV2 inverted terminal repeats (ITR), encapsidation signal (ψ), CAG promoter, optimized human AAT cDNA, and polyadenylation signal ($A_n$) was packaged into AAV5 or AAV5-PK2 capsid. D) Coomassie gel showing purified AAV5-PK2-AAT virus.
Figure 1B:
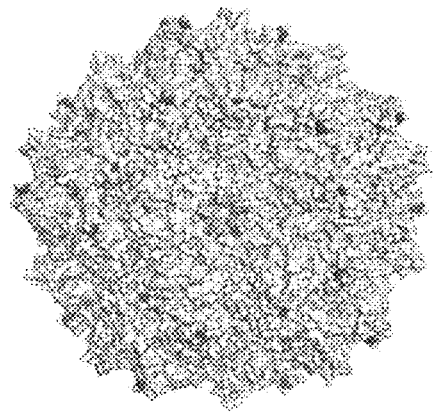
Figure 1C:
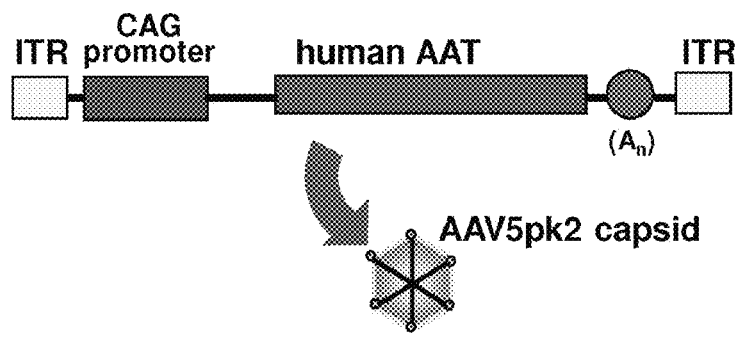
Figure 1D:
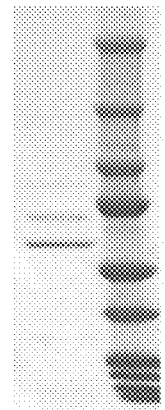
Figure 2:
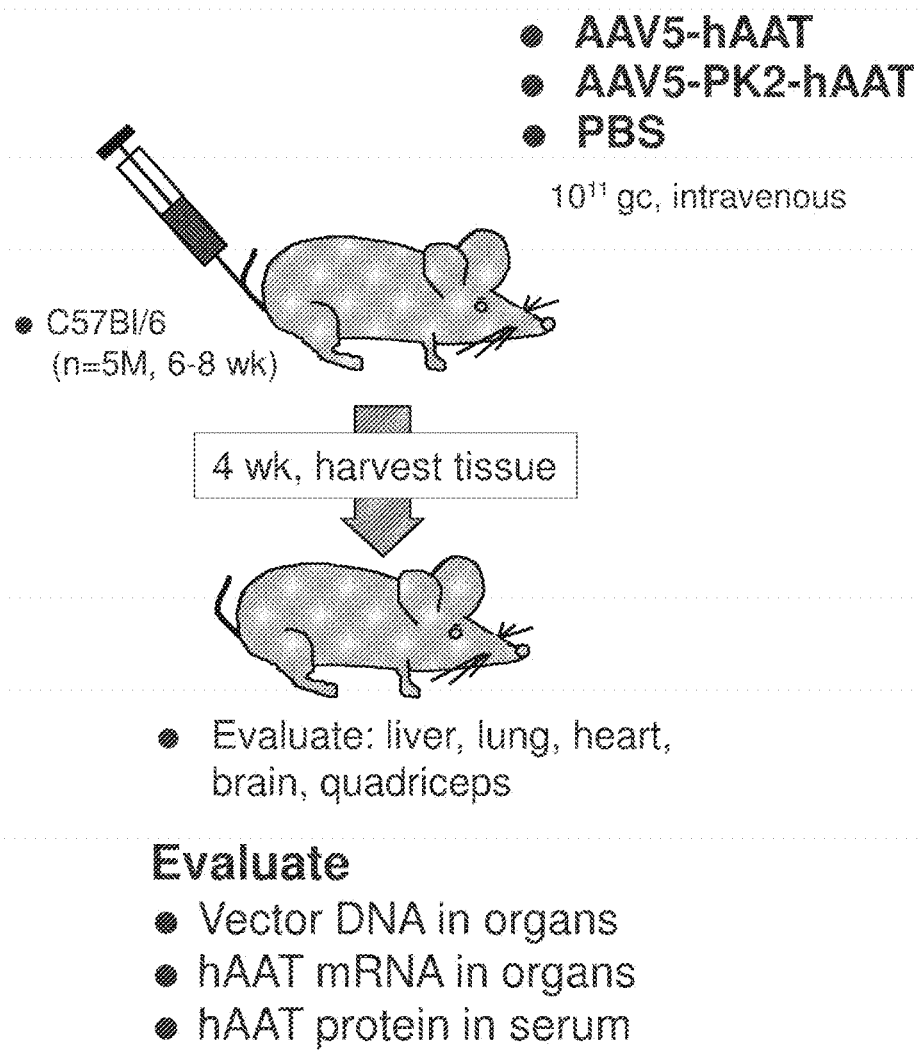
FIG. 2. Experimental protocol.
Figure 3A:
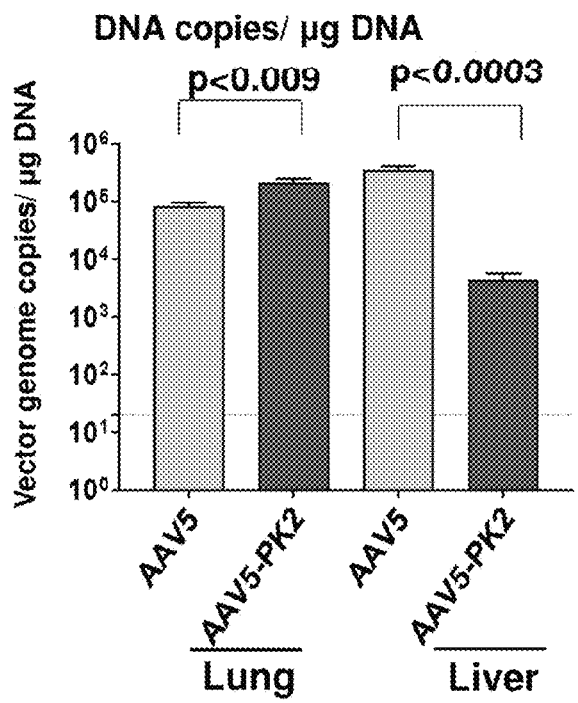
FIGS. 3A-D. Vector DNA distribution after intravenous administration of AAV5-hAAT and AAV5-PK2-hAAT. Whole organs were homogenized and DNA extracted for quantification by qRT-PCR. A) Vector genome copies per μg DNA in lung and liver. B) Vector genome copies per total tissue. C) Liver to lung ratio of vector genome copies per μg DNA. D) Liver to lung ratio of vector genome copies per total tissue.
Figure 3B:
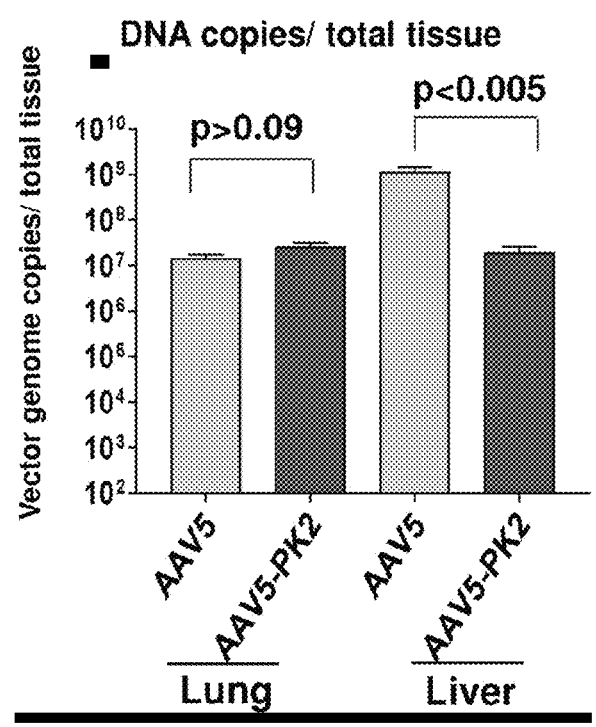
Figure 3C:
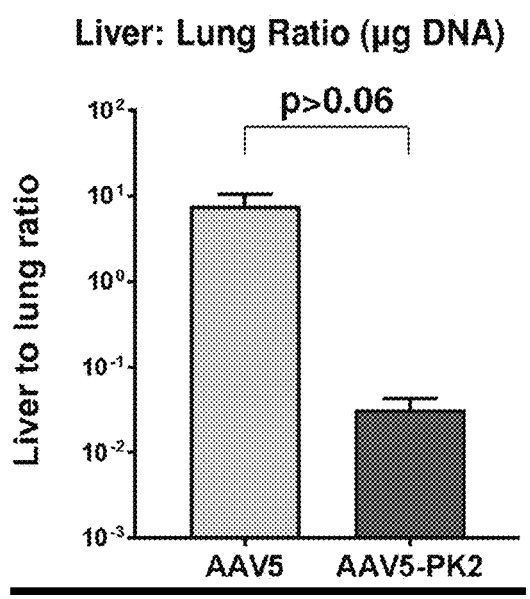
Figure 3D:
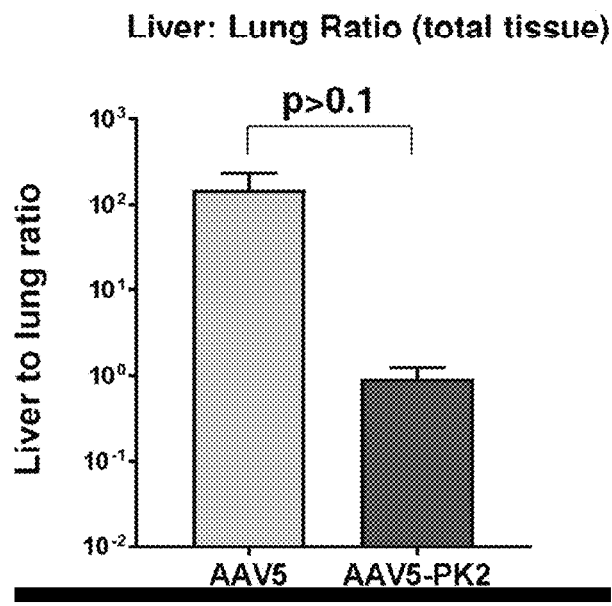
Figure 4A:
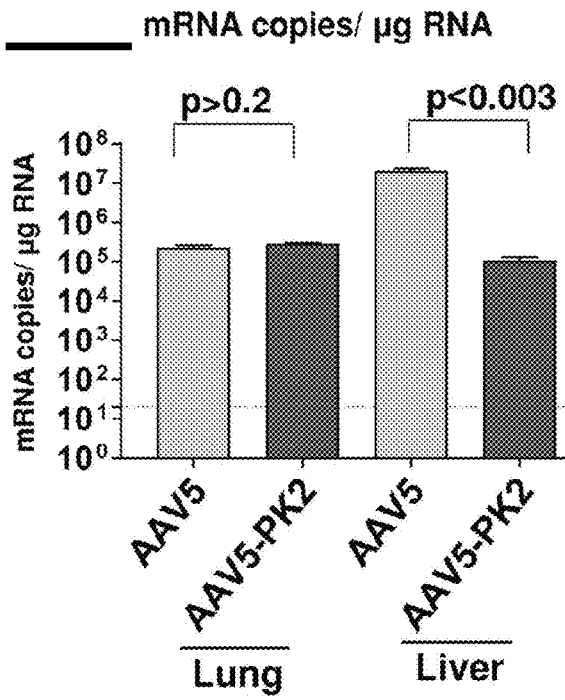
FIGS. 4A-D. hAAT mRNA distribution after intravenous administration of AAV5-hAAT and AAV5-PK2-hAAT. Whole organs were homogenized, RNA extracted, converted to cDNA, and quantified by qRT-PCR. A) hAAT mRNA copies per μg RNA in lung and liver. B) hAAT mRNA copies per total tissue. C) Liver to lung ratio of hAAT mRNA copies per μg RNA. D) Liver to lung ratio of hAAT mRNA copies per total tissue.
Figure 4B:
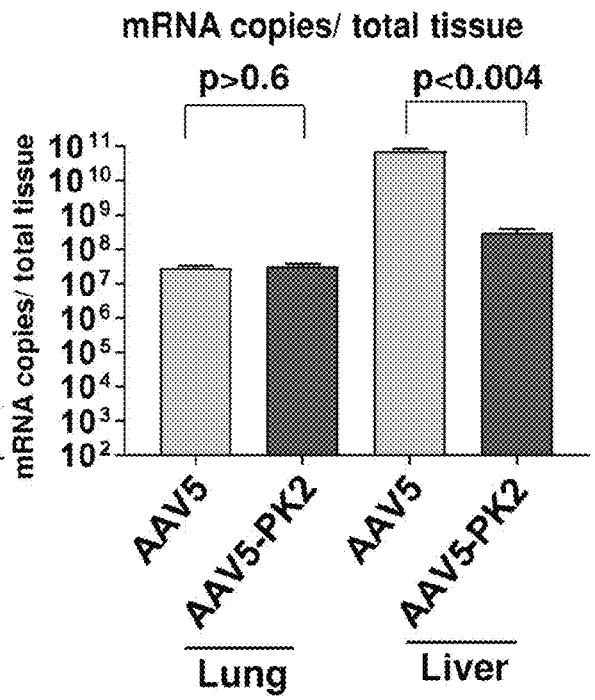
Figure 4C:
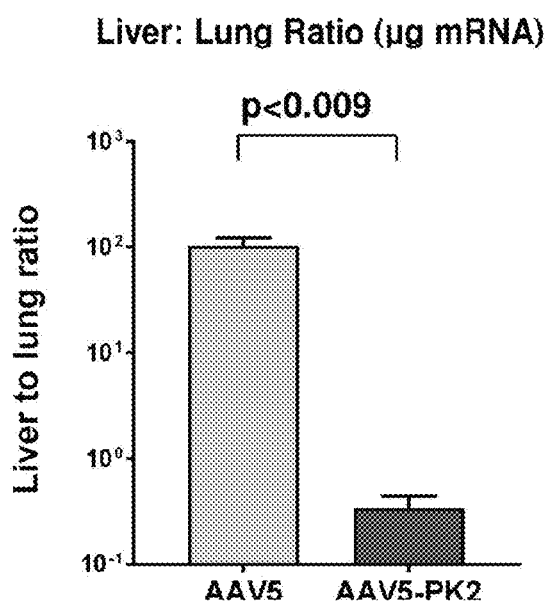
Figure 4D:
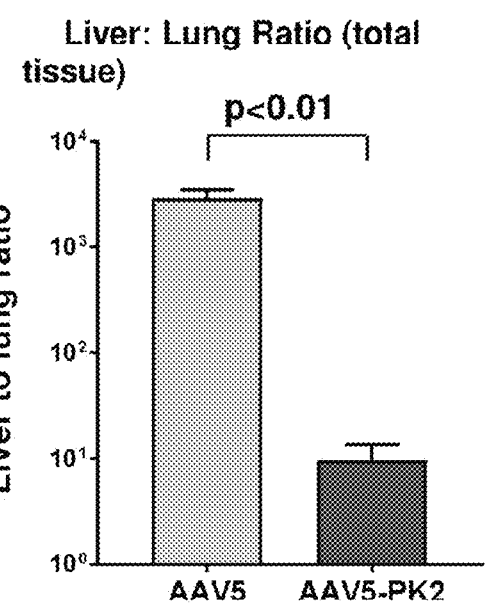
Figures 5A, 5B:
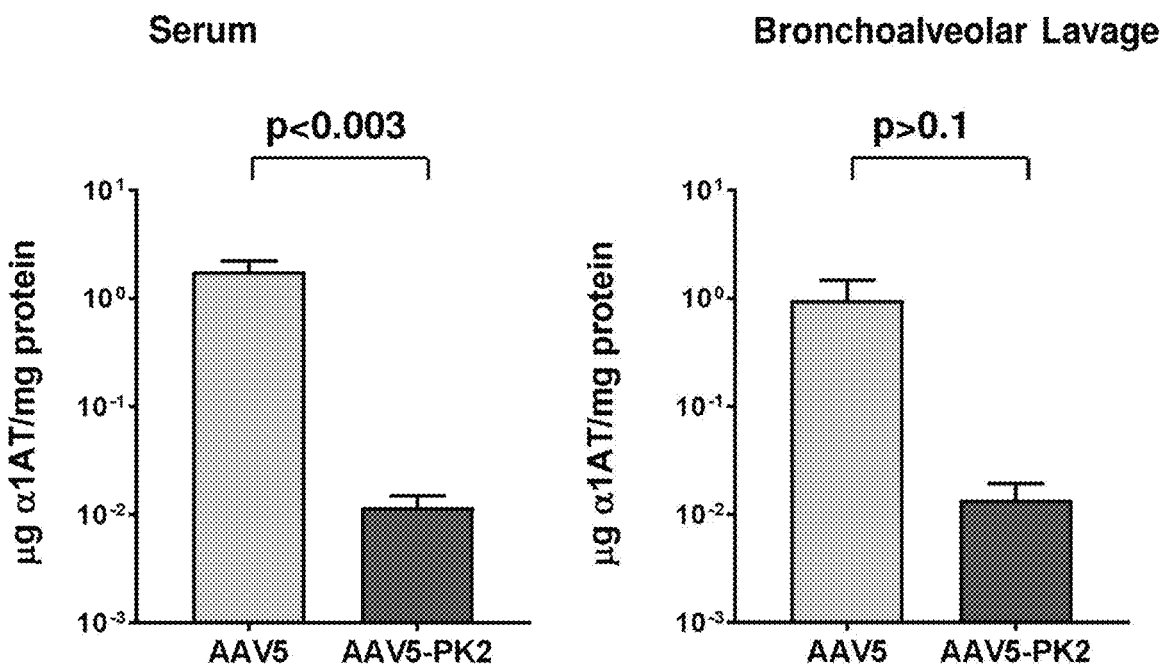
FIGS. 5A-C. hAAT protein in serum and BALF was quantified by ELISA after intravenous administration with AAV5-hAAT and AAV5-PK2-hAAT. A) hAAT serum levels per mg protein. B) hAAT BALF levels per mg protein. C) Ratio of BALF to serum hAAT (per mg protein).
Figure 5C:
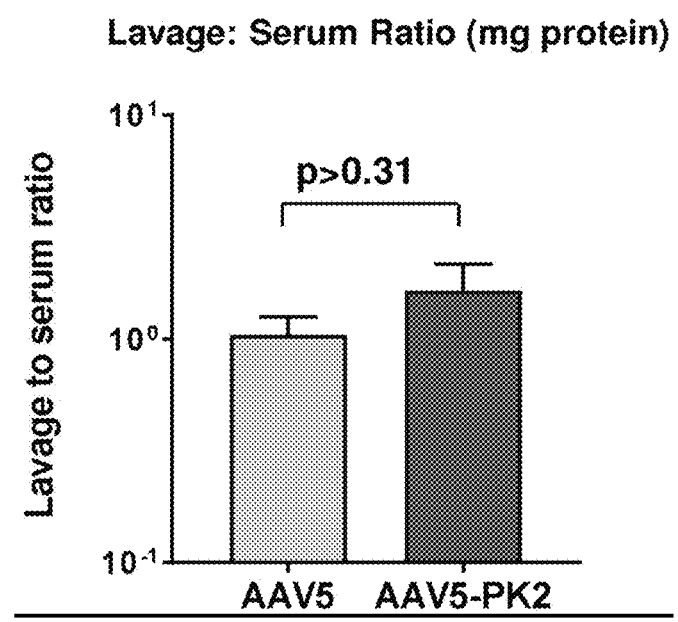
Figure 6A:
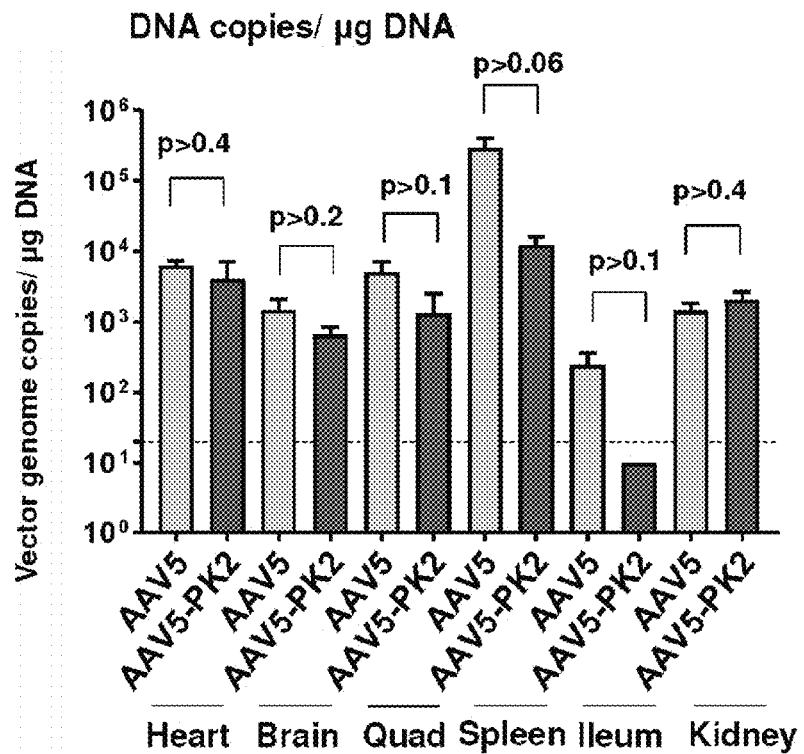
FIGS. 6A-B. Vector DNA distribution to other organs after intravenous administration of AAV5-hAAT and AAV5-PK2-hAAT. Whole organs were homogenized and DNA extracted for quantification by qRT-PCR. A) Vector genome copies per μg DNA in lung and liver. B) Vector genome copies per total tissue.
Figure 6B:
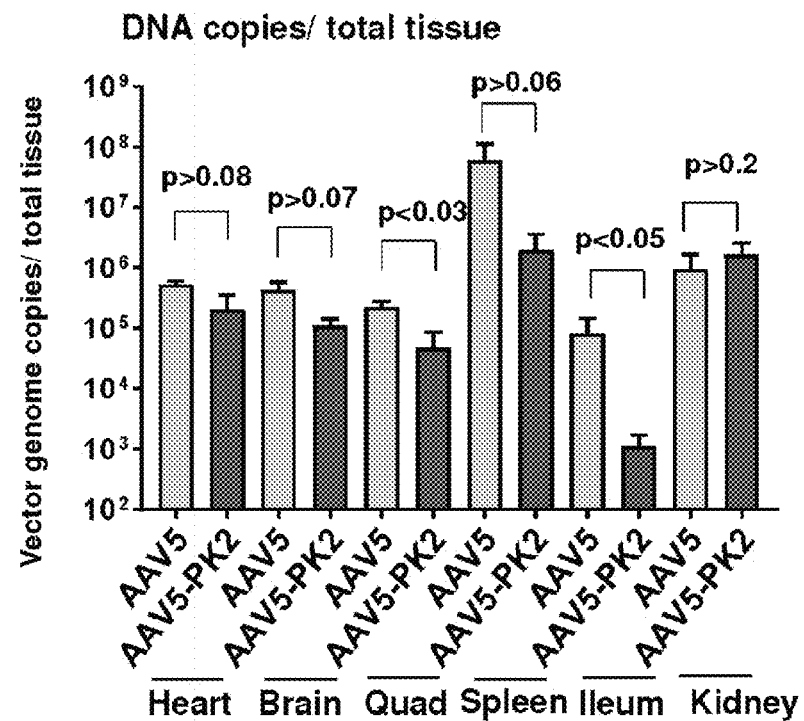

A "vector" refers to a macromolecule or association of macromolecules that comprises or associates with a polynucleotide, and which can be used to mediate delivery of the polynucleotide to a cell, either in vitro or in vivo. Illustrative vectors include, for example, plasmids, viral vectors, liposomes and other gene delivery vehicles. The polynucleotide to be delivered, sometimes referred to as a "target polynucleotide" or "transgene," may comprise a coding sequence of interest in gene therapy (such as a gene encoding a protein of therapeutic interest), a coding sequence of interest in vaccine development (such as a polynucleotide expressing a protein, polypeptide or peptide suitable for eliciting an immune response in a mammal), and/or a selectable or detectable marker.

"Transduction," "transfection," "transformation" or "transducing" as used herein, are terms referring to a process for the introduction of an exogenous polynucleotide into a host cell leading to expression of the polynucleotide, e.g., the transgene in the cell, and includes the use of recombinant virus to introduce the exogenous polynucleotide to the host cell. Transduction, transfection or transformation of a polynucleotide in a cell may be determined by methods well known to the art including, but not limited to, protein expression (including steady state levels), e.g., by ELISA, flow cytometry and Western blot, measurement of DNA and RNA by hybridization assays, e.g., Northern blots, Southern blots and gel shift mobility assays. Methods used for the introduction of the exogenous polynucleotide include well-known techniques such as viral infection or transfection, lipofection, transformation and electroporation, as well as other non-viral gene delivery techniques. The introduced polynucleotide may be stably or transiently maintained in the host cell.

"Gene delivery" refers to the introduction of an exogenous polynucleotide into a cell for gene transfer, and may encompass targeting, binding, uptake, transport, localization, replicon integration and expression.

"Gene transfer" refers to the introduction of an exogenous polynucleotide into a cell which may encompass targeting, binding, uptake, transport, localization and replicon integration, but is distinct from and does not imply subsequent expression of the gene.

"Gene expression" or "expression" refers to the process of gene transcription, translation, and post-translational modification.

An "infectious" virus or viral particle is one that comprises a polynucleotide component which it is capable of delivering into a cell for which the viral species is trophic. The term does not necessarily imply any replication capacity of the virus.

The term "polynucleotide" refers to a polymeric form of nucleotides of any length, including deoxyribonucleotides or ribonucleotides, or analogs thereof. A polynucleotide may comprise modified nucleotides, such as methylated or capped nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment described herein that is a polynucleotide encompasses both the double-stranded form and each of two complementary single-stranded forms known or predicted to make up the double-stranded form.

An "isolated" polynucleotide, e.g., plasmid, virus, polypeptide or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Isolated nucleic acid, peptide or polypeptide is present in a form or setting that is different from that in which h is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded). Enrichment can be measured on an absolute basis, such as weight per volume of solution, or it can be measured in relation to a second, potentially interfering substance present in the source mixture. Increasing enrichments of the embodiments may be preferred Thus, for example, a 2-fold enrichment, 10-fold enrichment, 100-fold enrichment, or a 1000-fold enrichment.

A "transcriptional regulatory sequence" refers to a genomic region that controls the transcription of a gene or coding sequence to which it is operably linked. Transcriptional regulatory sequences of use generally include at least one transcriptional promoter and may also include one or more enhancers and/or terminators of transcription.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in cis with the coding sequence, but it is not necessarily directly adjacent to it.

"Heterologous" means derived from a genotypically distinct entity from the entity to which it is compared. For example, a polynucleotide introduced by genetic engineering techniques into a different cell type is a heterologous polynucleotide (and, when expressed, can encode a heterologous polypeptide). Similarly, a transcriptional regulatory element such as a promoter that is removed from its native coding sequence and operably linked to a different coding sequence is a heterologous transcriptional regulatory element.

A "terminator" refers to a polynucleotide sequence that tends to diminish or prevent read-through transcription (i.e., it diminishes or prevent transcription originating on one side of the terminator from continuing through to the other side of the terminator). The degree to which transcription is disrupted is typically a function of the base sequence and/or the length of the terminator sequence. In particular, as is well known in numerous molecular biological systems, particular DNA sequences, generally referred to as "transcriptional termination sequences" are specific sequences that tend to disrupt read-through transcription by RNA polymerase, presumably by causing the RNA polymerase molecule to stop and/or disengage from the DNA being transcribed. Typical example of such sequence-specific terminators include poly-adenylation ("polyA") sequences, e.g., SV40 polyA. In addition to or in place of such sequence-specific terminators, insertions of relatively long DNA sequences between a promoter and a coding region also tend to disrupt transcription of the coding region, generally in proportion to the length of the intervening sequence. This effect presumably arises because there is always some tendency for an RNA polymerase molecule to become disengaged from the DNA being transcribed, and increasing the length of the sequence to be traversed before reaching the coding region would generally increase the likelihood that disengagement would occur before transcription of the coding region was completed or possibly even initiated. Terminators may thus prevent transcription from only one direction ("uni-directional" terminators) or from both directions ("bi-directional" terminators), and may be comprised of sequence-specific termination sequences or sequence-non-specific terminators or both. A variety of such terminator sequences are known in the art; and illustrative uses of such sequences within the context of the present disclosure are provided below.

"Host cells," "cell lines," "cell cultures," "packaging cell line" and other such terms denote higher eukaryotic cells, such as mammalian cells including human cells, useful in the present disclosure, e.g., to produce recombinant virus or recombinant fusion polypeptide. These cells include the progeny of the original cell that was transduced. It is understood that the progeny of a single cell may not necessarily be completely identical (in morphology or in genomic complement) to the original parent cell.

"Recombinant," as applied to a polynucleotide means that the polynucleotide is the product of various combinations of cloning, restriction and/or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter. Promoters include AAV promoters, e.g., P5, P19, P40 and AAV FIR promoters, as well as heterologous promoters.

An "expression vector" is a vector comprising a region which encodes a gene product of interest, and is used for effecting the expression of the gene product in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

The terms "polypeptide" and "protein" are used interchangeably herein to refer to polymers of amino acids of any length. The terms also encompass an amino acid polymer that has been modified; for example, disulfide bond formation, glycosylation, acetylation, phosphorylation, lipidation, or conjugation with a labeling component.

The term "exogenous," when used in relation to a protein, gene, nucleic acid, or polynucleotide in a cell or organism refers to a protein, gene, nucleic acid, or polynucleotide which has been introduced into the cell or organism by artificial or natural means. An exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells, or is otherwise flanked by a different nucleic acid sequence than that found in nature, e.g., an expression cassette which links a promoter from one gene to an open reading frame for a gene product from a different gene.

"Transformed" or "transgenic" is used herein to include any host cell or cell line, which has been altered or augmented by the presence of at least one recombinant DNA sequence. The host cells are typically produced by transfection with a DNA sequence in a plasmid expression vector, as an isolated linear DNA sequence, or infection with a recombinant viral vector.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of a selected sequence that is compared to some other sequence. Gaps (in either of the two sequences) are permitted to maximize matching; gap lengths of 15 bases or less are usually used, although 6 bases or less or 2 bases or less may be employed. When using oligonucleotides as probes or treatments, the sequence homology between the target nucleic acid and the oligonucleotide sequence is generally not less than 17 target base matches out of 20 possible oligonucleotide base pair matches (85%); not less than 9 matches out of 10 possible base pair matches (90%' or not less than 19 matches out of 20 possible base pair matches (95%).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less or 2 or less. Alternatively, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. The two sequences or parts thereof are more homologous if their amino acids are greater than or equal to 50% identical when optimally aligned using the ALIGN program.

The term "corresponds to" is used herein to mean that a polynucleotide sequence is structurally related to all or a portion of a reference polynucleotide sequence, or that a polypeptide sequence is structurally related to all or a portion of a reference polypeptide sequence, e.g., they have at least 80%, 85%, 90%, 95% or more, e.g., 99% or 100%, sequence identity. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, at least 90 to 95 percent sequence identity, or at least 99 percent sequence identity as compared to a reference sequence over a comparison window of at least 20 nucleotide positions, frequently over a window of at least 20-50 nucleotides, wherein the percentage of sequence identity is calculated by comparing the reference sequence to the polynucleotide sequence which may include deletions or additions which total 20 percent or less of the reference sequence over the window of comparison.

"Conservative" amino acid substitutions are, for example, aspartic-glutamic as polar acidic amino acids; lysine/arginine/histidine as polar basic amino acids; leucine/isoleucine/methionine/valine/alanine/glycine/proline as non-polar or hydrophobic amino acids; serine/threonine as polar or uncharged hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting polypeptide. Whether an amino acid change results in a functional polypeptide can readily be determined by assaying the specific activity of the polypeptide. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gin, his, lys, arg; (5) residues that influence chain orientation: gly, pro; and (6) aromatic; trp, tyr, phe.

The disclosure also envisions polypeptides with non-conservative substitutions. Non-conservative substitutions entail exchanging a member of one of the classes described above for another.

AAV Vectors with Modified Capsids

The disclosure provides an adeno-associated virus (AAV) vector which comprises a capsid that is modified to alter viral tropism and a viral genome. Adeno-associated virus is a member of the Parvoviridae family and comprises a linear, single-stranded DNA genome of less than about 5,000 nucleotides. AAV requires co-infection with a helper virus (i.e., an adenovirus or a herpes virus), or expression of helper genes, for efficient replication. AAV vectors used for administration of therapeutic nucleic acids typically have approximately 96% of the parental genome deleted, such that only the terminal repeats (ITRs), which contain recognition signals for DNA replication and packaging, remain. This eliminates immunologic or toxic side effects due to expression of viral genes. In addition, delivering specific AAV proteins to producing cells enables integration of the AAV vector comprising AAV ITRs into a specific region of the cellular genome, if desired (see, e.g., U.S. Pat. Nos. 6,342,390 and 6,821,511). Host cells comprising an integrated AAV genome show no change in cell growth or morphology (see, for example, U.S. Pat. No. 4,797,368).

The AAV ITRs flank the unique coding nucleotide sequences for the non-structural replication (Rep) proteins and the structural capsid (Cap) proteins (also known as virion proteins (VPs)). The terminal 145 nucleotides are self-complementary and are organized so that an energetically stable intramolecular duplex forming a T-shaped hairpin may be formed. These hairpin structures function as an origin for viral DNA replication by serving as primers for the cellular DNA polymerase complex. The Rep genes encode the Rep proteins Rep78, Rep68, Rep52, and Rep40. Rep78 and Rep68 are transcribed from the p5 promoter, and Rep 52 and Rep40 are transcribed from the p19 promoter. The Rep78 and Rep68 proteins are multifunctional DNA binding proteins that perform helicase and nickase functions during productive replication to allow for the resolution of AAV termini (see, e.g., Im et al., 1990). These proteins also regulate transcription from endogenous AAV promoters and promoters within helper viruses (see, e.g., Pereira et al., 1997). The other Rep proteins modify the function of Rep78 and Rep68. The cap genes encode the capsid proteins VP1, VP2, and VP3. The cap genes are transcribed from the p40 promoter.

The AAV vector may be generated using any AAV serotype known in the art. Several AAV serotypes and over 100 AAV variants have been isolated from adenovirus stocks or from human or nonhuman primate tissues (reviewed in, e.g., Wu et al., 2006). Generally, the AAV serotypes have genomic sequences of significant homology at the nucleic acid sequence and amino acid sequence levels, such that different serotypes have an identical set of genetic functions, produce virions which are essentially physically and functionally equivalent, and replicate and assemble by practically identical mechanisms. AAV serotypes 1-6 and 7-9 are defined as "true" serotypes, in that they do not efficiently cross-react with neutralizing sera specific for all other existing and characterized serotypes. Iii contrast, AAV serotypes 6, 10 (also referred to as Rh10), and 11 are considered "valiant" serotypes as they do not adhere to the definition of a "true" serotype. AAV serotype 2 (AAV2) has been used extensively for gene therapy applications due to its lack of pathogenicity, wide range of infectivity, and ability to establish long-term transgene expression (see, e.g., Carter, 2005; and Wu et al., supra). Genome sequences of various AAV serotypes and comparisons thereof are disclosed in, for example, GenBank Accession numbers U89790, J01901, AF043303, and AF085716; Chiorini et al., 1997; Srivastava et al., 1983; Chiorini et al., 1999; Rutledge et al., 1998; and Wu et al., 2000).

AAV rep and ITR sequences are particularly conserved across most AAV serotypes. For example, the Rep78 proteins of AAV2, AAV3A, AAV3B, AAV4, and AAV6 are reportedly about 89-93% identical (see Bantel-Schaal et al., 1999). It has been reported that AAV serotypes 2, 3A, 3B, and 6 share about 82% total nucleotide sequence identity at the genome level (Bantel-Schaal et al., supra). Moreover, the rep sequences and ITRs of many AAV serotypes are known to efficiently cross-complement functionally substitute) corresponding sequences from other serotypes during production of AAV particles in mammalian cells.

Generally, the cap proteins, which determine the cellular tropicity of the AAV particle, and related cap protein-encoding sequences, are significantly less conserved than Rep genes across different AAV serotypes. In view of the ability Rep and ITR sequences to cross-complement corresponding sequences of other serotypes, the AAV vector can comprise a mixture of serotypes and thereby be a "chimeric" or "pseudotyped" AAV vector. A chimeric AAV vector typically comprises AAV capsid proteins derived from two or more (e.g., 2, 3, 4, etc.) different AAV serotypes. In contrast, a pseudotyped AAV vector comprises one or more ITRs of one AAV serotype packaged into a capsid of another AAV serotype. Chimeric and pseudotyped AAV vectors are further described in, for example, U.S. Pat. No. 6,723,551; Flotte, 2006; Gao et al., 2004; Gao et al., 2002; De et al., 2006; and Gao et al., 2006.

In one embodiment, the AAV vector is generated using an AAV that infects humans (e.g., AAV2). Alternatively, the AAV vector is generated using an AAV that infects non-human primates, such as, for example, the great apes (e.g., chimpanzees), Old World monkeys (e.g., macaques), and New World monkeys (e.g., marmosets). In one embodiment, the AAV vector is generated using an AAV that infects a non-human primate pseudotyped with an AAV that infects humans. Examples of such pseudotyped AAV vectors are disclosed in, e.g., Cearley et al., *Molecular Therapy*, 13:528 (2006). In one embodiment, an AAV vector can be generated which comprises a capsid protein from an AAV that infects rhesus macaques pseudotyped with AAV2 inverted terminal repeats (ITRs). In a particular embodiment, the AAV vector comprises a capsid protein from AAV10 (also referred to as "AAVrh.10"), which infects rhesus macaques pseudotyped with AAV2 ITRs (see, e.g., Watanabe et al., 2010; and Mao et al., 2011).

A large number of promoters may be used in the viral genome or in a helper virus free system, e.g., to express viral capsid, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, and the RSV promoter. Inducible promoters include, for example, the Tet system (U.S. Pat. Nos. 5,464,758 and 5,814,618), the Ecdysone inducible system (No et al., 1996), the T-REX™ system (invitrogen, Carlsbad, CA), LACSWITCH™ System (Stratagene, San Diego, CA), and the Cre-ERT tamoxifen inducible recombinase system (Indra et al., 1999; U.S. Pat. No. 7,112,715; and Kramer & Fussenegger, 2005).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences.

Typically AAV vectors are produced using well characterized plasmids. For example, human embryonic kidney 293T cells are transfected with one of the transgene specific plasmids and another plasmid containing the adenovirus helper and AAV rep and cap genes (specific to AAVrh.10, 8 or 9 as required). After 72 hours, the cells are harvested and the vector is released from the cells by five freeze/thaw cycles. Subsequent centrifugation and benzonase treatment removes cellular debris and unencapsidated DNA. Iodixanol gradients and ion exchange columns may be used to further purify each AAV vector. Next, the purified vector is concentrated by a size exclusion centrifuge spin column to the required concentration. Finally, the buffer is exchanged to create the final vector products formulated (for example) in 1× phosphate buffered saline. The viral titers may be measured by TaqMan® real-time PCR and the viral purity may be assessed by SDS-PAGE.

Pharmaceutical Compositions and Delivery

The disclosure provides a composition comprising, consisting essentially of, or consisting of the above-described gene transfer vector and a pharmaceutically acceptable (e.g., physiologically acceptable) carrier. When the composition consists essentially of the inventive gene transfer vector and a pharmaceutically acceptable carrier, additional components can be included that do not materially affect the composition (e.g., adjuvants, buffers, stabilizers, anti-inflammatory agents, solubilizers, preservatives, etc.). When the composition consists of the inventive gene transfer vector and the pharmaceutically acceptable carrier, the composition does not comprise any additional components. Any suitable carrier can be used within the context of the disclosure, and such carriers are well known in the art. The choice of carrier will be determined, in part, by the particular site to which the composition may be administered and the particular method used to administer the composition. The composition optionally can be sterile with the exception of the gene transfer vector described herein. The composition can be frozen or lyophilized for storage and reconstituted in a suitable sterile carrier prior to use. The compositions can be generated in accordance with conventional techniques described in, e.g., *Remington: The Science and Practice of Pharmacy,* 21st Edition, Lippincott Williams & Wilkins, Philadelphia, PA (2001).

Suitable formulations for the composition include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. In one embodiment, the carrier is a buffered saline solution. In one embodiment, the inventive gene transfer vector is administered in a composition formulated to protect the gene transfer vector from damage prior to administration. For example, the composition can be formulated to reduce loss of the gene transfer vector on devices used to prepare, store, or administer the gene transfer vector, such as glassware, syringes, or needles. The composition can be formulated to decrease the light sensitivity and/or temperature sensitivity of the gene transfer vector. To this end, the composition may comprise a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the gene transfer vector, facilitate administration, and increase the efficiency of the inventive method. Formulations for gene transfer vector-containing compositions are further described in, for example, Wright et al, 2003 and Wright et al., 2005).

The composition also can be formulated to enhance transduction efficiency. In addition, one of ordinary skill in the art will appreciate that the inventive gene transfer vector can be present in a composition with other therapeutic or biologically-active agents. For example, factors that control inflammation, such as ibuprofen or steroids, can be part of the composition to reduce swelling and inflammation associated with in vivo administration of the gene transfer vector. Immune system stimulators or adjuvants, e.g., interleukins, lipopolysaccharide, and double-stranded RNA, can be administered to enhance or modify an immune response. Antibiotics, i.e., microbicides and fungicides, can be present to treat existing infection and/or reduce the risk of future infection, such as infection associated with gene transfer procedures.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

In certain embodiments, a formulation may comprise a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

The composition can be administered in or on a device that allows controlled or sustained release, such as a sponge, biocompatible meshwork, mechanical reservoir, or mechanical implant. Implants (see, e.g., U.S. Pat. No. 5,443,505), devices see, e.g., U.S. Pat. No. 4,863,457), such as an implantable device, e.g., a mechanical reservoir or an implant or a device comprised of a polymeric composition, are particularly useful for administration of the inventive gene transfer vector. The composition also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

Delivery of the compositions comprising the inventive gene transfer vectors may be intracerebral (including but not limited to intraparenchymal, intraventricular, or intracisternal), intrathecal (including but not limited to lumbar or cisterna magna), or systemic, including but not limited to intravenous, or any combination thereof using devices known in the art. Delivery may also be via surgical implantation of an implanted device.

The dose of the gene transfer vector in the composition administered to the mammal will depend on a number of factors, including the size (mass) of the mammal, the extent of any side-effects, the particular route of administration, and the like. In one embodiment, the inventive method comprises administering a "therapeutically effective amount" of the composition comprising the inventive gene transfer vector described herein. A "therapeutically effective amount" refers to an amount effective, at dosages and for periods of time necessary, to achieve a desired therapeutic result. The therapeutically effective amount may vary according to factors such as the extent of pathology, age, sex, and weight of the individual, and the ability of the gene transfer vector to elicit a desired response in the individual. The dose of gene transfer vector in the composition required to achieve a particular therapeutic effect typically is administered in units of vector genome copies per cell (gc/cell) or vector genome copies/per kilogram of body weight (gc/kg). One of ordinary skill in the art can readily determine an appropriate gene transfer vector dose range to treat a patient having a particular disease or disorder, based on these and other factors that are well known in the art. The therapeutically effective amount may be between $1\times10^{10}$ genome copies to $1\times10^{13}$ genome copies.

In one embodiment, the composition is administered once to the mammal. It is believed that a single administration of the composition will result in persistent expression in the mammal with minimal side effects. However, in certain cases, it may be appropriate to administer the composition multiple times during a therapeutic period to ensure sufficient exposure of cells to the composition. For example, the composition may be administered to the mammal two or more times (e.g., 2, 3, 4, 5, 6, 6, 8, 9, or 10 or more times) during a therapeutic period.

Exemplary Capsid Proteins for Modification

In one embodiment, AAV capsid proteins, may have at least 50%, 55%, 60%, 65%, 70%, 75%, 80%, 85%, 90%, 92%, 95%, 96%, 97%, 98% or 99% amino acid sequence identity to a reference AAV capsid polypeptide sequence, e.g., have at least 50%, 55%, 60%, 65%, 70%, 75%, 80%, 85%, 90%, 92%, 95%, 96%, 97%, 98% or 99% amino acid sequence identity to an AAV capsid sequence, such as a capsid sequence of e.g., an AAV-1, AAV-2, AAV-3, AAV-4, AAV-5, AAV-6, AAV-7, AAV-8, AAV-9, AAV-10, AAV-11 or AAV-12, and including pseudotyped viruses and non-natural serotypes such as AAV-DJ (Grimm et al., 2008), and AAV-PHP.eB or AAV-PHP.S (Chan et al., 2017). In one embodiment, the capsid sequence may have at least 50%, 55%, 60%, 65%, 70%, 70%, 75%, 800%, 85%, 90%, 92%, 95%, 96%, 97%, 98% or 99% amino acid sequence identity to any of SEQ ID Nos. 17-21:

```
AAV2 VP1
                                                              (SEQ ID NO: 17)
      1    maadgylpdw ledtlsegir qwwklkpgpp ppkpaerhkd dsrglvlpgy kylgpfngld 61    kgepvneada aalehdkayd rqldsgdnpy lkynhadaef qerlkedtsf ggnlgravfq 121    akkrvleplg lveepvktap gkkrpvehsp vepdsssgtg kagqqparkr lnfgqtgdad 181    svpdpqplgq ppaapsglgt ntmatgsgap madnnegadg vgnssgnwhc dstwmgdrvi 241    ttstrtwalp tynnhlykqi ssqsgasndn hyfgystpwg yfdfnrfhch fsprdwqrli 301    nnnwgfrpkr lnfklfniqv kevtqndgtt tiannltstv qvftdseyql pyvlgsahqg 361    clppfpadvf mvpqygyltl nngsqavgrs sfycleyfps qmlrtgnnft fsytfedvpf 421    hssyahsqsl drlmnplidq ylyylsrtnt psgtttqsrl qfsqagasdi rdqsrnwlng 481    pcyrqqrvsk tsadnnnsey swtgatkyhl ngrdslvnpg pamashkdde ekffpqsgvl 541    ifgkqgsekt nvdiekvmit deeeirttnp vateqygsvs tnlqrgnrqa atadvntqgv
```

-continued

```
601    lpgmvwqdrd vylqgpiwak iphtdghthp splmggfglk hpppqilikn tpvpanpstt
661    fsaakfasfi tqystgqvsv eiewelqken skrwnpeiqy tsnynksvnv dftvdtngvy
721    seprpigtry ltrnl
```

AAV8 VP 1
(SEQ ID NO: 18)
```
  1    maadgylpdw lednlsegir ewwalkpgap kpkanqqkqd dgrglvlpgy kylgpfngld
 61    kgepvnaada aalehdkayd qqlqagdnpy lrynhadaef qerlqedtsf ggnlgravfq
121    akkrvleplg lveegaktap gkkrpvepsp qrspdsstgi gkkgqqpark rlnfgqtgds
181    esvpdpqplg eppaapsgvg pntmaaggga pmadnnegad gvgsssgnwh cdstwlgdrv
241    ittstrtwal ptynnhlykq isngtsggat ndntyfgyst pwgyfdfnrf hchfsprdwq
301    rlinnnwgfr pkrlsfklfn iqvkevtqne gtktiannlt stiqvftdse yqlpyvlgsa
361    hqgclppfpa dvfmipqygy ltlnngsqav grssfycley fpsqmlrtgn nfqftytfed
421    vpfhssyahs qsldrlmnpl idqylyylsr tqttggtant qtlgfsqggp ntmanqaknw
481    lpgpcyrqqr vstttgqnnn snfawtagtk yhlngrnsla npgiamathk ddeerffpsn
541    gilifgkqna ardnadysdv mltseeeikt tnpvateeyg ivadnlqqqn tapqigtvns
601    qgalpgmvwq nrdvylqgpi wakiphtdgn fhpsplmggf glkhpppqil ikntpvpadp
661    pttfnqskln sfitqystgq vsveiewelq kenskrwnpe iqytsnyyks tsvdfavnte
721    gvyseprpig tryltrnl
```

AAV7 VP1
(SEQ ID NO: 19)
```
  1    maadgylpdw lednlsegir ewwdlkpgap kpkanqqkqd ngrglvlpgy kylgpfngld
 61    kgepvnaada aalehdkayd qqlkagdnpy lrynhadaef qerlqedtsf ggnlgravfq
121    akkrvleplg lveegaktap akkrpvepsp qrspdsstgi gkkgqqpark rlnfgqtgds
181    esvpdpqplg eppaapssvg sgtvaaggga pmadnnegad gvgnasgnwh cdstwlgdrv
241    ittstrtwal ptynnhlykq issetagstn dntyfgystp wgyfdfnrfh chfsprdwqr
301    linnnwgfrp kklrfklfni qvkevttndg vttiannlts tiqvfsdsey qlpyvlgsah
361    qgclppfpad vfmipqygyl tlnngsqsvg rssfycleyf psqmlrtgnn fefsysfedv
421    pfhssyahsq sldrlmnpli dqylyylart qsnpggtagn relqfyqggp stmaeqaknw
481    lpgpcfrqqr vsktldqnnn snfawtgatk yhlngrnslv npgvamathk ddedrffpss
541    gvlifgktga tnkttlenvl mtneeeirpt npvateeygi vssnlqaant aaqtqvvnnq
601    galpgmvwqn rdvylqgpiw akiphtdgnf hpsplmggfg lkhpppqili kntpvpanpp
661    evftpakfas fitqystgqv sveiewelqk enskrwnpei qytsnfekqt gvdfavdsqg
721    vyseprpigt ryltrnl
```

AAV-5 VP1
(SEQ ID NO: 20)
```
  1    msfvdhppdw leevgeglre flgleagppk pkpnqqhqdq arglvlpgyn ylgpgngldr
 61    gepvnradev arehdisyne qleagdnpyl kynhadaefq ekladdtsfg gnlgkavfqa
121    kkrvlepfgl veegaktapt gkriddhfpk rkkarteeds kpstssdaea gpsgsqqlqi
181    paqpasslga dtmsaggggp lgdnnqgadg vgnasgdwhc dstwmgdrvv tkstrtwvlp
241    synnhqyrei ksgsvdgsna nayfgystpw gyfdfnrfhs hwsprdwqrl innywgfrpr
301    slrvkifniq vkevtvqdst ttiannltst vqvftdddyq lpyvvgngte gclpafppqv
361    ftlpqygyat lnrdntenpt ersstfcley fpskmlrtgn nfeftynfee vpfhssfaps
421    qnlfklanpl vdqylyrfvs tnntggvqfn knlagryant yknwfpgpmg rtqgwnlgsg
481    vnrasvsafa ttnrmelega syqvppqpng mtnnlqgsnt yalentmifn sqpanpgtta
```

```
541    tylegnmlit  sesetqpvnr  vaynvggqma  tnnqssttap  atgtynlqei  vpgsvwmerd 601    vylqgpiwak  ipetgahfhp  spamggfglk  hpppmmlikn  tpvpgnitsf  sdvpvssfit 661    qystgqvtve  mewelkkens  krwnpeiqyt  nnyndpqfvd  fapdstgeyr  ttrpigtryl 721    trpl
```

AAV-5
```
                                                                  (SEQ ID NO: 21)
  1    msfvdhppdw  leevgeglre  flgleagppk  pkpnqqhqdq  arglvlpgyn  ylgpgngldr 61    gepvnradev  arehdisyne  qleagdnpyl  kynhadaefq  ekladdtsfg  gnlgkavfqa 121    kkrvlepfgl  veegaktapt  gkriddhfpk  rkkarteeds  kpstssdaea  gpsgsqqlqi 181    paqpasslga  dtmsaggggp  lgdnnqgadg  vgnasgdwhc  dstwmgdrvv  tkstrtwvlp 241    synnhqyrei  ksgsvdgsna  nayfgystpw  gyfdfnrfhs  hwsprdwqrl  innywgfrpr 301    slrvkifniq  vkevtvqdst  ttiannltst  vqvftdddyq  lpyvvgngte  gclpafppqv 361    ftlpqygyat  lnrdntenpt  erssffcley  fpskmlrtgn  nfeftynfee  vpfhssfaps 421    qnlfklanpl  vdqylyrfvs  tnntggvqfn  knlagryant  yknwfpgpmg  rtqgwnlgsg 481    vnrasvsafa  ttnrmelega  syqvppqpng  mtnnlqgsnt  yalentmifn  sqpanpgtta 541    tylegnmlit  sesetqpvnr  vaynvggqma  tnnqssttap  atgtynlqei  vpgsvwmerd 601    vylqgpiwak  ipetgahfhp  spamggfglk  hpppmmlikn  tpvpgnitsf  sdvpvssfit 661    qystgqvtve  mewelkkens  krwnpeiqyt  nnyndpqfvd  fapdstgeyr  ttrpigtryl 721    trpl.
```

Dosages, Formulations and Routes of Administration

Administration of the recombinant viruses may be continuous or intermittent, depending, for example, upon the recipient's physiological condition, whether the purpose of the administration is therapeutic or prophylactic, and other factors known to skilled practitioners. The administration of the recombinant viruses may be essentially continuous over a preselected period of time or may be in a series of spaced doses. Both local and systemic administration is contemplated. When the recombinant viruses are employed for prophylactic purposes, recombinant viruses are amenable to chronic use, e.g., by systemic administration.

One or more suitable unit dosage forms comprising the recombinant viruses, can be administered by a variety of routes including oral, or parenteral, including by rectal, transdermal, subcutaneous, intravenous, intramuscular, intraperitoneal, intrathoracic, intrapulmonary and intranasal routes. For example, for administration to the liver, intravenous administration may be employed. For administration to the lung, airway administration may be employed. The formulations may, where appropriate, be conveniently presented in discrete unit dosage forms and may be prepared by any of the methods well known to pharmacy. Such methods may include the step of bringing into association the recombinant viruses with liquid carriers, solid matrices, semi-solid carriers, finely divided solid carriers or combinations thereof, and then, if necessary, introducing or shaping the product into the desired delivery system.

When the recombinant viruses are prepared for oral administration, they may be combined with a pharmaceutically acceptable carrier, diluent or excipient to form a pharmaceutical formulation, or unit dosage form. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Pharmaceutical formulations containing the recombinant viruses can be prepared by procedures known in the art using well known and readily available ingredients. For example, the recombinant viruses can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The recombinant viruses can also be formulated as elixirs or solutions for convenient oral administration or as solutions appropriate for parenteral administration, for instance by intramuscular, subcutaneous or intravenous routes.

The pharmaceutical formulations of the recombinant viruses can also take the form of an aqueous or anhydrous solution or dispersion, or alternatively the form of an emulsion or suspension.

Thus, the recombinant viruses may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$-$C_4$ alkyl esters of short-chain acids, e.g., ethyl or isopropyl lactate, fatty acid triglycerides such as the products marketed under the name "Miglyol", isopropyl myristate, animal, mineral and vegetable oils and polysiloxanes.

For administration to the upper (nasal) or lower respiratory tract by inhalation, the recombinant viruses are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the recombinant viruses may be administered via nose drops, a liquid spray, such as via a plastic bottle atomizer or metered-dose inhaler. Typical of atomizers are the Mistometer (Wintrop) and the Medihaler (Riker).

The local delivery of the recombinant viruses can also be by a variety of techniques which administer the agent at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The formulations and compositions described herein may also contain other ingredients such as antimicrobial agents, or preservatives. Furthermore, the active ingredients may also be used in combination with other agents, for example, bronchodilators.

The recombinant viruses may be administered to a mammal alone or in combination with pharmaceutically acceptable carriers. As noted above, the relative proportions of active ingredient and carrier are determined by the solubility and chemical nature of the compound, chosen route of administration and standard pharmaceutical practice.

The dosage of the recombinant viruses will vary with the form of administration, the particular compound chosen and the physiological characteristics of the particular patient under treatment. Generally, small dosages will be used initially and, if necessary, will be increased by small increments until the optimum effect under the circumstances is reached.

Exemplary Doses

An effective amount of virus is administered, depending on the objectives of treatment. An effective amount may be given in single or divided doses. Where a low percentage of transduction can cure a genetic deficiency, then the objective of treatment is generally to meet or exceed this level of transduction. In some instances, this level of transduction can be achieved by transduction of only about 1 to 5% of the target cells, but is more typically 20% of the cells of the desired tissue type, usually at least about 50%, at least about 80%, at least about 95?, or at least about 99% of the cells of the desired tissue type. As a guide, the number of vector particles present in a single dose given by bronchoscopy will generally be at least about $1 \times 10^{12}$, e.g., about $1 \times 10^{13}$, $1 \times 10^{14}$, $1 \times 10^{15}$ or $1 \times 10^{16}$ particles, including both DNAse-resistant and DNAse-susceptible particles. In terms of DNAse-resistant particles, the dose will generally be between $1 \times 10^{12}$ and $1 \times 10^{16}$ particles, more generally between about $1 \times 10^{12}$ and $1 \times 10^{15}$ particles.

Exemplary Gene Products

In one embodiment, the gene product is a therapeutic gene product, e.g., GM-CSF, CD40L, IL-2, CD80, MDA-7, or TNF-alpha. In one embodiment, the gene product is a prophylactic gene product, e.g. kallikrein or is pathogen-derived protein fragments (Pestivirus E2, *C. psittaci* MOMP, *S. aureus* FnBP, *S. aureus* ClfA, Avian paramyxovirus HN, *B. melitensis* OMP-31, *S. japonicum* Sj23). In one embodiment, the gene product is a catalytic RNA. In one embodiment the gene product is a guide RNA. In one embodiment the gene is a donor for homologous recombination. In one embodiment the gene product is a nuclease suitable for genome editing, e.g. TALENS, *S. pyogenes* Cas9, *S. aureus* Cas9. In one embodiment, the gene product is a cytotoxic gene product, e.g., suicide genes such as rexin-G or HSVtk in combination with ganciclovir, an apoptosis inducer, e.g., p53, p27Kip1, p21Waf1, p16INK4A, Ad5IkB, or cyclin-dependent kinase inhibitors, or an angiogenesis inhibitor. In one embodiment, the gene product is a chimeric T-cell receptor (anti-CD19 scfv/CD28/CD3ζ CAR, anti-BCMA scfv/4-1BB/CD3ζ CAR).

In one embodiment, the gene to be delivered includes but is not limited to cystic fibrosis transmembrane conductance regulator, α-antitrypsin, β-globin, γ-globin, tyrosine hydroxylase, glucocerebrosidase, aryl sulfatase A, factor VIII, dystrophin or erythropoietin, a viral, bacterial, tumor or fungal antigen, or an immune response modulator, e.g., a cytokine including but not limited to IFN-alpha, IFN-gamma, TNF, IL-1, IL-17, or IL-6.

Exemplary Insertions or Substitutions

In one embodiment, the insertion includes 1, 2, 3, or 4 lysines. In one embodiment, the insertion has formula (I):

X1-X2-X3-X4 (SEQ ID NO:22), and wherein at least one of X1-X4 is lysine (K) and at least one of the other residues is A, G, V, T, I, S or M; wherein at least two of X1-X4 are lysine (K) and the other residues are A, G, V, T, I, S or M; wherein at least one of X1-X4 is lysine (K) and at least one of the other residues is C, S, D, E, N, Q, or R; wherein at least two of X1-X4 are lysine (K) and the other residues are C, S, M, D, E, Q, or R; wherein at least one of X1-X4 is lysine (K) and at least one of the other residues is H, P, Y, W or F; or wherein at least two of X1-X4 are lysine (K) and the other residues are H, P, Y, W or F. In one embodiment, the insertion is 5 or fewer residues. In one embodiment, the insertion is 4 or fewer residues. In one embodiment, the insertion does not have R. In one embodiment, the insertion does not have F. In one embodiment, the insertion does not have N. In one embodiment, the insertion does not have Q.

In one embodiment, the substitution includes 1, 2, 3, 4 or 5 lysines. In one embodiment, the substitution results in formula (II): Z1-Z2-Z3-Z4-Z5-Z6-Z7-Z8-Z9-Z10-Z11-Z12-Z13 (SEQ ID NO:23), and wherein at least one of Z1-Z13 is lysine (K) and the other residues include A, G, V, T, I, S, M, C, D, E, N, Q, H, P, Y, W or F; wherein at least two of Z1-Z13 are lysine (K) and the other residues include A, G, V, T, I, S, E, N, Q, H, P, Y, W or F; wherein at least three of Z1-Z13 are lysine (K) and the other residues include A, G, V, T, I, S, M, C, D, E, N, Q, H, P, Y, W or F; or wherein at least four of Z1-Z13 are lysine (K) and the other residues include A, G, V, T, I, S, C, Q, H, P, Y, W or F.

In one embodiment, the substitution includes 1, 2, 3, 4 or 5 lysines. In one embodiment, the substitution results in formula (II): Z1-Z2-Z3-Z4-Z5-Z6-Z7-Z8-Z9-Z10-Z11-Z12-Z13 (SEQ NO: 22), and wherein at least one of Z1-Z13 is lysine (K) and the other residues include A, G, V, T, I, S, M, D, E, N, Q, H, P, or Y; wherein at least two of Z1-Z13 are lysine (K) and the other residues include A, G, V, T, I, S, M, D, E, N, Q, H, P, or wherein at least three of Z1-Z13 are lysine (K) and the other residues include A, G, V, T, I, S, NI, D, E, N, Q, H, P, or Y; or wherein at least four of Z1-Z13 are lysine (K) and the other residues include A, G, V, T, I, S, M, D, E, N, Q, H, P, or Y.

The invention will be further described by the following non-limiting example.

Example

Intravenous administration of all naturally occurring adeno-associated virus (AAV) vectors are liver tropic, with the majority of the total vector dose mediating gene expression in liver hepatocytes. Specificity and transduction levels are serotype dependent. To design an AAV vector to de-target liver but enhance delivery to lung following intravenous administration, modifications were made to the AAV capsid to direct the tropism of the virus, e.g., adding additional positively charged lysine residues to the AAV capsid would enhance the ability of the virus to adhere to negatively charged cell surface molecules such as heparan sulfate proteoglycans, leading to enhanced transduction of the organ representing the first capillary bed encountered. To test this hypothesis, using site directed mutagenesis, two lysine residues were inserted into variable loop VIII of the AAV serotype 5 capsid of a vector coding for human α1-antitrypsin (AAV5-PK2-hAAT). The site for insertion was at position 575 (see Hida et al., 2010), which is located on a loop with variable amino acid sequence and is exposed on the surface of the capsid. For example, two lysine residues were inserted after residue 575. That insertion results in an additional 120 lysine residues on the AAV5 capsid.

Distribution of the vector and vector expression was quantified following administration of $10^{11}$ genome copies (gc) of AAV5-PK2-hAAT or the identical vector with the AAV5 wild-type capsid (AAV5-hAAT) by the intravenous route to C57Bl/6 male mice. Four wk post-administration, organs were harvested, and vector DNA and mRNA quantified by TagMan. Consistent with the experience for all naturally occurring AAV vectors, intravenous administration of AAV5-hAAT resulted in the highest vector DNA levels in the liver (ratio of vector DNA in liver to lung 150±71; liver to heart 452±169; and liver to skeletal muscle 4260±1800). hAAT mRNA levels in the various organs paralleled the vector DNA distribution. In striking contrast, following intravenous administration of the AAV5-PK2-hAAT vector, the liver to lung vector DNA ratio was 0.17±0.06 (p=0.03, compared to the wild type capsid), liver to heart 84±48, (p=0.03) and liver to skeletal muscle 671±319, p=(0.04). The lysine-modified vector was de-targeted from the liver, resulting in 61-fold lower (p=0.003) liver and 2.3-fold higher (p=0.03) lung vector DNA levels compared to the wild-type capsid (lung to liver DNA ratio 276-fold higher, p=0.04). The hAAT mRNA levels paralleled the vector DNA levels. Serum AAT levels were 84±20 μg/ml for AAV5-hAAT and only 0.57±0.15 μg/ml for AAV5-PK2-hAAT supporting the de-targeting of AAV5-PK2-hAAT to the liver, the main producer of secreted proteins such as hAAT.

Thus, with the identical dose administered iv, for AAV5 there was 80-fold more vector DNA in liver than lung per μg DNA, and 59-fold more vector DNA in liver than lung per total tissue, and AAV5-PK2 had 2.6-fold more vector DNA in lung than liver per μg DNA, and 1.8-fold more vector DNA in lung than liver per total tissue. Therefore, the liver was de-targeted. Moreover, serum levels of hAAT from mice administered AAV5-PK2-hAAT were 152-fold lower than AAV5-hAAT but BAL levels were only 70-fold lower, confirming enhanced hAAT expression from AAV5-PK2-hAAT in the lung.

For AAV5 there was 197-fold more hAAT mRNA in liver than lung per μg RNA, and 242-fold more in liver than lung per total tissue. In contrast, AAV5-PK2 had 1.3-fold more hAAT mRNA in lung than liver per μg DNA, and 1.2-fold more hAAT mRNA in lung than liver per total tissue.

In summary, genetic modification of the AAV capsid with lysine residues results in a "sticky" vector that transduces the organ containing the first capillary bed encountered following intravenous administration (the lung), thus shifting the targeting of the vector away from the liver. This capsid modification strategy with lysine residues should be applicable to all AAV vectors, and depending on the administration route, useful for targeting AAV vectors to specific organs, and also useful from a safety viewpoint for limiting "spill" of vector to the systemic circulation and other organs, thereby targeting specific organs via the route of administration.

After intravenous administration, the AAV5-PK2 vector was also de-targeted from the spleen and ileum. With the identical dose administered iv, AAV5-hAAT had 32-fold more vector DNA in the spleen and 75-fold more vector DNA in the ileum than AAV5-PK2-hAAT.

REFERENCES

Bantel-Schaal et al., *J. Virol.,* 73(2):939 (1999).
Carter, *Hum. Gene Ther.,* 16:541 (2005);
Cearley et al., *Molecular Therapy,* 13:528 (2006). I
Chan et al., *Nat. Neurosci.,* 20:1174 (2017).

Chiorini et al., *J. Virol.*, 71:6823 (1997).
Chiorini et al., *J. Virol.*, 73:1309 (1999).
Dalkara et al. 2013. *Sci Transl Med* 5, 189ra76
De et al., *Mol. Ther.*, 13:67 (2006).
Flotte, *Mol. Ther.*, 13(1):1 (2006).
Gao et al., *J. Virol.*, 78:6381 (2004).
Gao et al., *Mol. Ther.*, 13:77 (2006).
Gao et al., *Proc. Natl. Acad. Sci. USA*, 99:11854 (2002).
Govindasamy et al. 2013. *J. Virol.* 87(20): 11187-99.
Grimm et al., *J. Virol.*, 82:5887 (2008).
Hida et al., 2010 *Arch. Biochem. Biophys.*, 496:1.
Im et al., *Cell*, 61:447 (1990)).
Indra et al, *Nuc. Acid. Res.*, 27:4324 (1999).
Indra et al, *Nuc. Acid. Res.*, 28:e99 (2000).
Judd et al. 2012. *Mol Ther-Nuc Acids* 1, e54
Khabou et al. 2016. *Biotechnol Bioeng* 113(12):2717-2724).
Kramer &. Fussenegger, *Methods Mol. Biol.*, 308:123 (2005)).
Mao et al., *Hunt. Gene Therapy*, 22:1525 (2011).
No et al., *Proc. Natl. Acad. Sci.*, 93:3346 (1996)).
Pereira et al., *J. Virol.*, 71:1079 (1997)).
Rutledge et al., *J. Virol.*, 72:309 (1998).
Srivastava et al., *J. Virol.*, 45:555 (1983).
Watanabe et al., *Gene Ther.*, 17(8):1042 (2010).
Wright et at, *Curr. Opin. Drug Discov. Devel.*, 6(2): 174-178 (2003).
Wright et al., *Molecular Therapy*, 12: 171-178 (2005).).
Wu et al., *J. Virol.*, 74:8635 (2000)).
Wu et al., *Molecular Therapy*, 14(3): 316 (2006)).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An infectious recombinant adeno-associated virus (rAAV) with altered tropism, comprising: a recombinant AAV genome and a modified AAV capsid that provides the altered tropism and which is capsid altered relative to a corresponding rAAV without the modification in the AAV capsid, wherein the modified AAV capsid comprises i) an insertion of one or more positively charged amino acid residues in a portion of the AAV capsid that is exposed to the surface, or ii) a substitution of one or more non-positively charged amino acid residues with one or more positively charged amino acid residues in a portion of the AAV capsid that is exposed to the surface, wherein at least one of the positively charged residues in i) or ii) or both is a lysine, wherein the portion of the capsid that is modified is loop VIII.

2. The virus of claim 1, wherein 2, 3, 4, 5, 6, 7, 8, 9, 10 or up to 20 amino acids are substituted.

3. The virus of claim 1, wherein 5 or fewer amino acids are substituted with positively charged amino acid residues.

4. The virus of claim 1, wherein the insertion comprises 2, 3, 4, 5, 6, 7, 8, 9, 10 or up to 20 amino acids.

5. The virus of claim 1, wherein 5 or fewer amino acids are inserted.

6. The virus of claim 1, wherein two or more positively charged amino acid residues are substituted or inserted.

7. The virus of claim 6, wherein at least two of the positively charged residues are adjacent to each other.

8. The virus of claim 1, wherein the positively charged residues further comprise arginine.

9. The virus of claim 1, wherein the modification comprises at least two lysine residues.

10. The virus of claim 1, wherein the AAV is AAV2, AAV3, AAV4, AAV5, AAV6, AAV7, AAV8, AAV9, or AAVrh10.

11. The virus of claim 1, wherein the rAAV recombinant genome comprises at least one expression cassette for a prophylactic or therapeutic gene product.

12. A method to prevent, inhibit or treat a disorder or disease in a mammal, comprising administering to a mammal in need thereof a composition comprising an amount of the virus of claim 1 effective to prevent, inhibit or treat the disorder or disease.

13. The method of claim 12, wherein the mammal is a human.

14. The method of claim 12, wherein the composition is systemically administered.

15. The method of claim 12, wherein the composition is intravenously administered.

16. The method of claim 12, wherein one or more lysine residues are inserted at a position in loop VIII comprising TNNQSSTTAPATG (SEQ ID NO:4).

17. The method of claim 12, wherein the capsid modification enhances delivery to an organ other than liver.

18. The method of claim 12, wherein the modification enhances delivery to the lung.

19. The method of claim 12, wherein the modification enhances delivery to an organ relative to the corresponding rAAV without the modification.

* * * * *